(12) United States Patent
Jain

(10) Patent No.: US 8,608,688 B2
(45) Date of Patent: Dec. 17, 2013

(54) CATHETER APPARATUS

(75) Inventor: Ajay Kumar Jain, London (GB)

(73) Assignee: Barts and the London NHS Trust, Greater London (GB)

( * ) Notice: Subject to any disclaimer, the term of this patent is extended or adjusted under 35 U.S.C. 154(b) by 360 days.

(21) Appl. No.: 12/738,831

(22) PCT Filed: Oct. 17, 2008

(86) PCT No.: PCT/GB2008/003522
§ 371 (c)(1),
(2), (4) Date: Jul. 15, 2010

(87) PCT Pub. No.: WO2009/050478
PCT Pub. Date: Apr. 23, 2009

(65) Prior Publication Data
US 2010/0280450 A1    Nov. 4, 2010

(30) Foreign Application Priority Data

Oct. 19, 2007  (GB) .................................. 0720561.0
May 12, 2008  (GB) .................................. 0808589.6

(51) Int. Cl.
*A61M 29/00* (2006.01)

(52) U.S. Cl.
USPC ........................................................ 604/96.01

(58) Field of Classification Search
USPC ......................... 604/536, 528; 623/1.27, 1.35
See application file for complete search history.

(56) References Cited

U.S. PATENT DOCUMENTS

| 4,248,224 A |   | 2/1981 | Jones |
|---|---|---|---|
| 5,423,311 A | * | 6/1995 | Snoke et al. .................. 600/109 |
| 5,720,735 A |   | 2/1998 | Dorros |
| 5,873,852 A | * | 2/1999 | Vigil et al. ..................... 604/509 |

* cited by examiner

*Primary Examiner* — Nicholas Lucchesi
*Assistant Examiner* — Melissa A Snyder
(74) *Attorney, Agent, or Firm* — Steptoe & Johnson LLP

(57) ABSTRACT

A catheter apparatus is provided with lumens for accommodating guidewires. The apparatus comprises an actuator controllable to move the distal ends of the lumens relative to each other. Accordingly, the separation of the guidewires can be controlled, enabling probing by the guidewires of different area of an occlusion in a blood vessel, such as a chronic total occlusion.

33 Claims, 16 Drawing Sheets

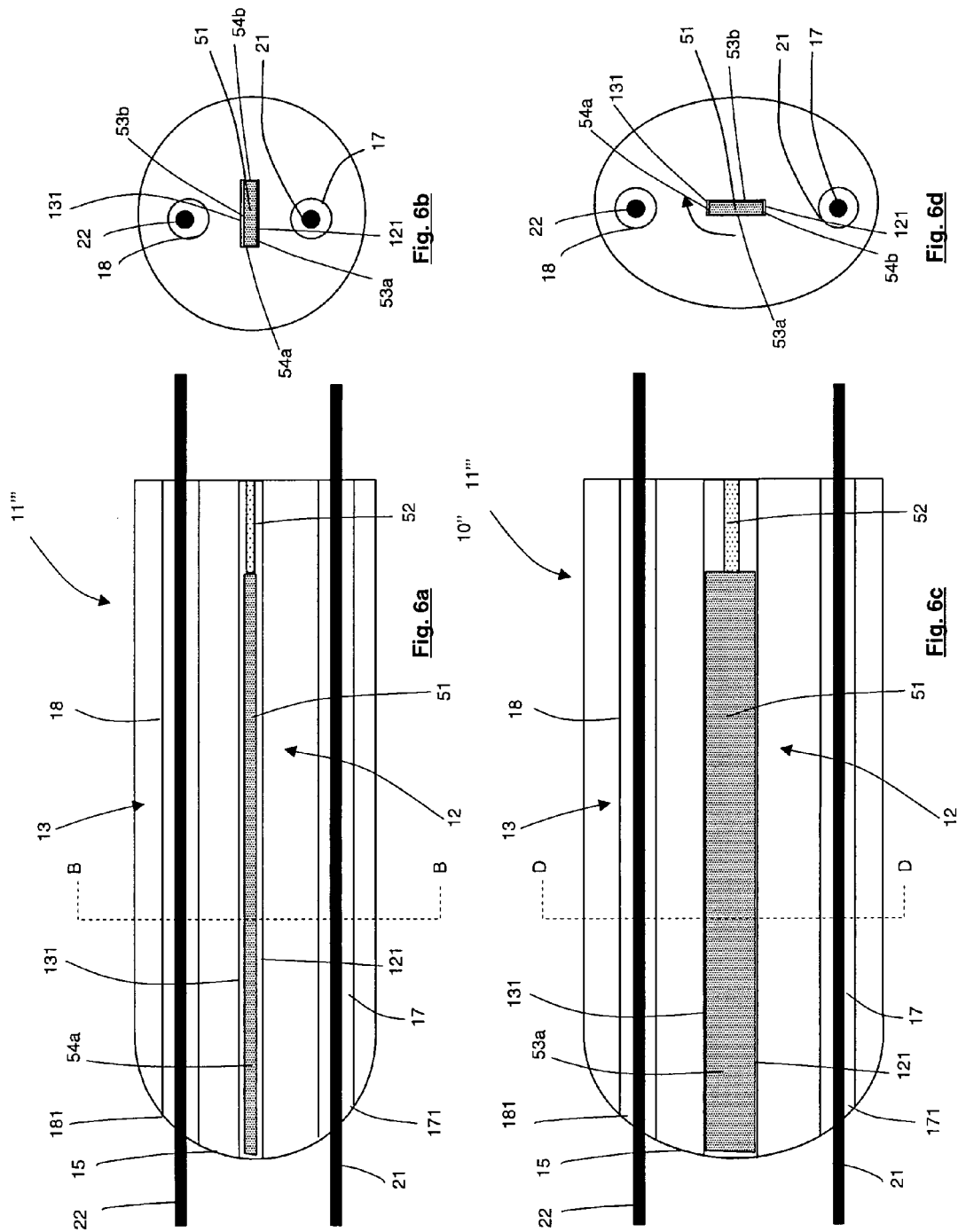

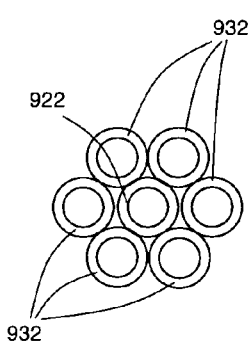
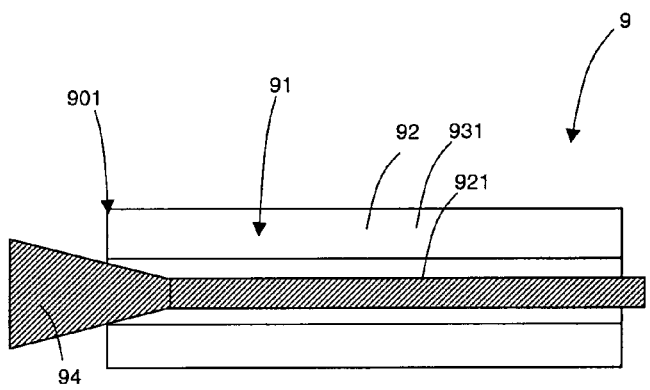
Fig. 11a    Fig. 11b
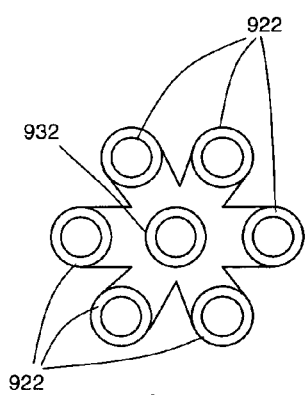
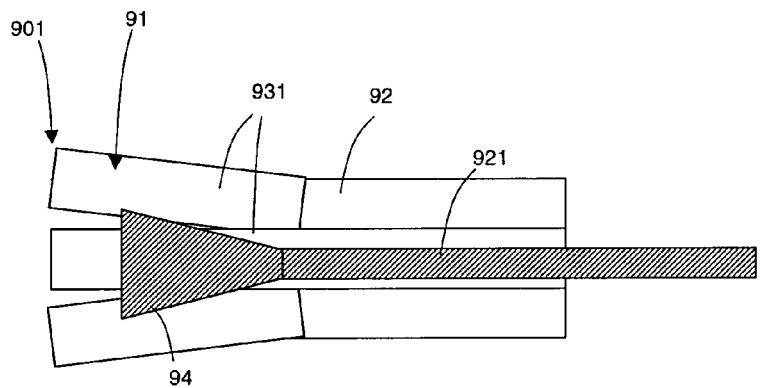
Fig. 12a    Fig. 12b

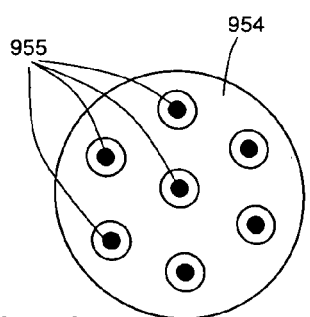
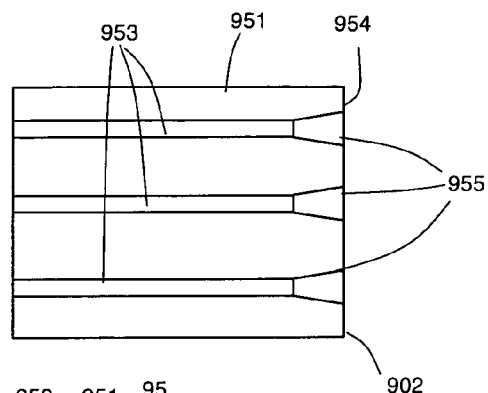
Fig. 17b    Fig. 17c
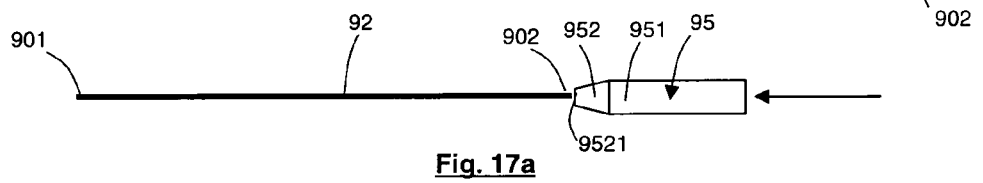
Fig. 17a
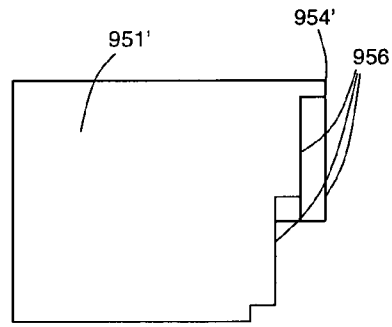
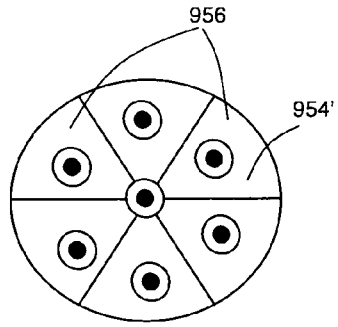
Fig. 18a    Fig. 18b
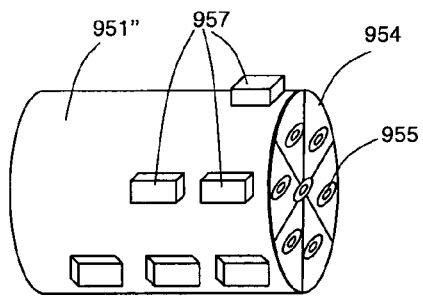
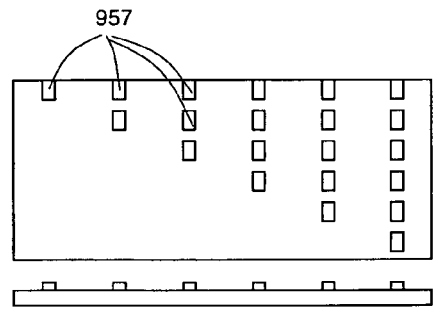
Fig. 19a    Fig. 19b

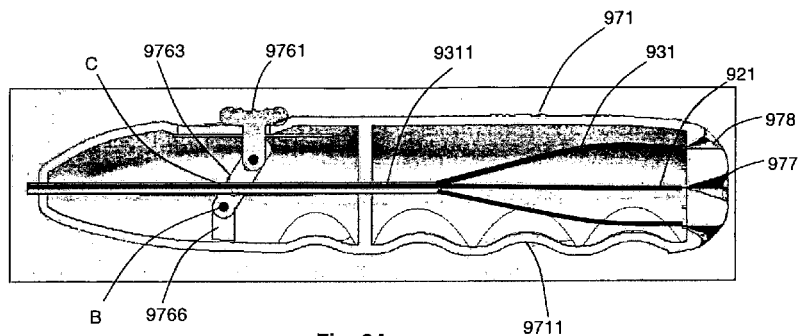
Fig. 24
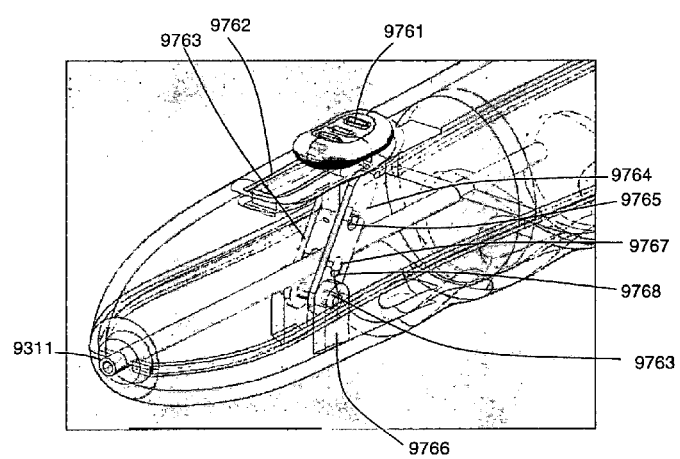
Fig. 25
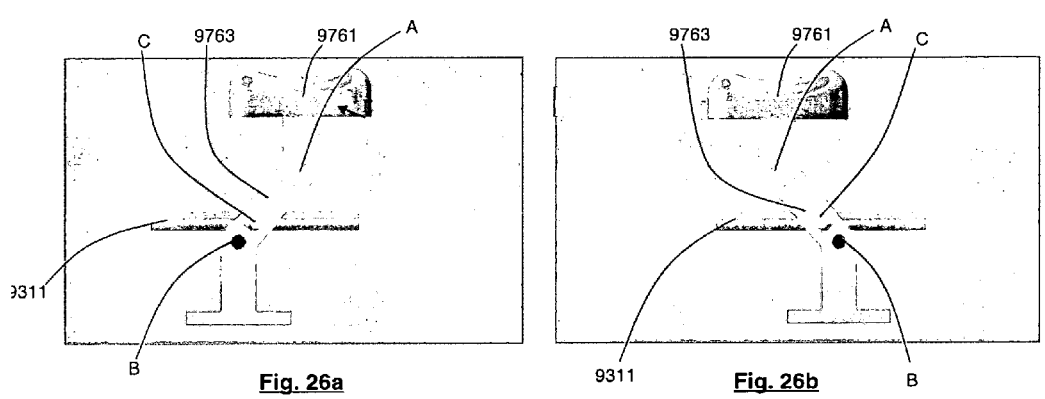
Fig. 26a
Fig. 26b

CATHETER APPARATUS

CROSS-REFERENCE TO RELATED APPLICATIONS

This application claims priority to International Application No. PCT/GB2008/003522, filed on Oct. 17, 2008, which claims priority to Great Britain Patent Application No. 0720561.0, filed Oct. 19, 2007, which claims priority to Great Britain Patent Application No. 0808589.6, filed May 12, 2008, each of which is incorporated by reference in its entirety.

This invention relates to catheter apparatus, particularly, but not necessarily exclusively, catheter apparatus for the treatment of chronic total occlusions.

A chronic total occlusion (CTO) is a blockage in a blood vessel, which is typically more than three months old, formed due to the build up of atherosclerotic plaque in the blood vessel wall, narrowing the path through the blood vessel and ultimately closing it off, preventing blood flow through the vessel.

Patient's with CTOs suffer symptoms such as angina and myocardial infarction, leading to a high level of morbidity. If a CTO is reopened there is known to be a benefit in terms of reduced morbidity and mortality.

Currently, coronary artery bypass graft (CABG) surgery is the preferred treatment of a CTO, which works by establishing blood flow round the CTO. However, bypass surgery is invasive, complex, expensive and not without risk to the patient. In view of this, in some cases, percutaneous transluminal coronary angioplasty (PTCA) are employed.

Typically, PTCAs involve specialist guidewire exchange at the CTO site. For example, a guide catheter is sent to the proximal part of the coronary artery, and a stiff guidewire is then passed down the catheter towards the CTO. The wire is then used to probe the calcified cap of the CTO to either find a pathway, such as a microvessel, through the CTO, or penetrate the cap of the CTO and allow a new pathway through the CTO to be established.

Once the thin guidewire has successfully crossed the CTO, a balloon catheter is passed along the guiding wire and through the CTO. The inserted balloon is then inflated; crushing the calcification and plaque against the vessel wall. A stent can then be inserted into the open vessel and expanded in an attempt to ensure the vessel remains open.

Known devices employing guidewires for the treatment of CTO's include the "Conquest" device by Asahi Intecc Co., Ltd. and the "Crosswire™" device by Terumo Medical Corportation. These devices employ stiff guidewires to increase the pushability of the guidewires to facilitate crossing of the CTO; however, the increased stiffness limits the ability of the wire to find an appropriate path through the CTO, and because of their stiffness may of themselves cause complications.

Other known guidewires employ microcatheters to stabilize guidewires. For example, microcatheters are used in Ev3 Inc.'s "Echelon™", Boston Scientific "Excelsior®" and St. Jude Medical, Inc.'s "Venture™", relating to US2005/0209559. Abbott Laboratory's "Asahi Tornus®" is a modified guide wire.

Microcatheters add support to the wire. However, with the exception of St. Jude Medical, Inc.'s "Venture™", they do not allow, in situ, any alteration in the direction of travel of the guide wire, meaning that it is difficult to probe different areas of the CTO with the guidewire in order to find an appropriate path through the CTO.

St. Jude Medical, Inc.'s "Venture™" has a microcatheter which uses wires embedded in the catheter which can be pushed and pulled in order to steer the tip of the catheter, and thus a guidewire extending through the catheter. However, it has been found that the response of the catheter tip to steering can be difficult to predict.

Alternative known devices for treating CTOs include Lumend Inc.'s Frontrunner® device, relating to US2005/0222595, which uses expansion tongs to break up the CTO via blunt microdissection. However, this device is complicated and expensive, and may cause dissection of the blood vessel wall, potentially leading to vessel rupture.

FlowCardia Inc's Crosser™ device, relating to U.S. Pat. No. 6,942,677, is used to re-canalize CTOs and relies on a monorail catheter delivering vibrational energy to facilitate the crossing of CTOs. Although considered less traumatic than the Frontrunner®, it suffers similar problems, and relies on an expensive control system.

IntraLuminal Therapeutics, Inc.'s Safe-Cross® device, relating to U.S. Pat. No. 6,852,109, uses optical coherence reflectometry which provides information on the cap of the CTO, to enable the user to probe the guidewire at an optimal area of the CTO. However, this device has been found to be difficult to use and expensive.

According to a first aspect of the present invention, there is provided a catheter apparatus, the catheter apparatus having a proximal end and a distal end, the distal end being for insertion into a patient's body, the catheter apparatus comprising:
  a catheter having a proximal end and a distal end;
  first and second lumens for accommodating first and second guidewires respectively, each lumen comprising a distal opening, the distal openings of the first and second lumens being moveable relative to each other; and
  an actuator for controllably changing the separation between the distal openings of the first and second lumens.

One or both of the first and second lumens may be provided within the catheter, whereupon the distal openings of the first and/or second lumens are preferably provided at the distal end of the catheter. As an alternative, the apparatus may comprise an additional section, e.g., a tube, in which one of the first and second lumens is provided. This may provide what is known as a 'rapid exchange lumen'. The additional section is preferably fixed to the catheter, and may extend alongside the catheter from a position at the distal end of the catheter, along all or part of the length of the catheter.

Since the actuator can change the separation between the distal openings, the separation between the first and second guidewires, which can project from the distal openings, can also be changed accordingly.

According to a second aspect of the present invention, there is provided a catheter apparatus, the catheter apparatus having a proximal end and a distal end, the distal end being for insertion into a patient's body, the catheter apparatus comprising:
  a catheter having a proximal end and a distal end;
  first and second guidewires, the guidewires arranged to project at the distal end of the catheter apparatus, and
  an actuator for controllably changing the separation between the guidewires at the distal end of the catheter apparatus.

Preferably, the first and second guidewires are disposed in first and second lumen, which may be arranged as described above with respect to the first aspect of the invention.

In the first and second aspects, preferably the first guide wire is an introducer guidewire for guiding the apparatus to a destination in the patient's body and preferably the second guide wire is a work wire for probing and passing through an occlusion, e.g. a CTO, in a blood vessel. Since the separation between the second guide wire and the first guidewire can be adjusted, the second guidewire can probe different areas of the calcified cap of the CTO in order to find an appropriate pathway, e.g. a microvessel, through the CTO. Once through, a balloon catheter may be inserted through the pathway to widen the pathway. The inserted balloon can then be inflated, crushing the calcification and plaque of the CTO against the vessel wall. A stent can then be inserted into the open vessel and expanded to ensure the vessel remains open, and allow blood flow beyond the previous occlusion.

By changing the separation between the first and second guidewires, the second guidewire can be probed along a generally linear surface section of the CTO. However, preferably the catheter is controllably rotatable. For example, the catheter, and thus the second guidewire, may be controllably rotatable about the longitudinal axis of the first guidewire. Accordingly, a substantially circular or annular surface section of the CTO may be swept out and probed in a controlled manner by the second guidewire. The first and second guidewires may be swapped between the first and second lumens.

Preferably, the catheter has a tip region at its distal end comprising first and second sections, the first and second sections being moveable relative to each other, the distal openings of the first and second lumens being located in the first and second sections respectively, wherein the actuator is arranged to change the separation between the first and second sections in order to change the separation between the distal openings of the first and second lumen.

The tip region of the catheter may comprise catheter side walls which are split, to permit separation of the first and second sections. Alternatively, the tip region of the catheter may have catheter sidewalls which are flexible, to permit separation of the first and second sections.

Preferably, the first and second sections, first and second lumen and/or first and second guide wires are biased toward a position in which they are close together. The actuator may be arranged to push or pull, or repel or attract, the first and second sections, first and second lumens and/or first and second guide wires apart in order to change the separation between the guidewires.

As the separation between the guidewires changes, the longitudinal axes of the first and second guidewires may remain in alignment, e.g., parallel alignment, or the longitudinal axes may converge or diverge from each other as they project from the distal end of the catheter apparatus.

Preferably, the actuator comprises an expandable device, for example an inflatable balloon. The expandable element may be arranged to press against the first and second lumens, the first and second sections and/or the first and second guidewires, such that, when expanded, it pushes the first and second guidewires apart. The expandable device may be expanded and contracted to vary the separation of the first and second guidewires as required. By using an inflatable balloon as the expandable device, the separation of the first and second guidewires can be controlled precisely by inflation and deflation of the balloon. The balloon may be comprised in a balloon catheter, which extends to the proximal end of the catheter apparatus for control by a user, e.g. a doctor or clinician.

As an alternative, the actuator may comprise a moveable wedge element. The wedge element may be moveable into a position between the first and second sections, the first and second lumens and/or the first and second guidewires in order to push the guidewires apart, and moveable away from the this position in order to allow the guidewires to move closer together. Preferably, the wedge element is attached to an elongate control element, e.g. a guidewire, which extends to the proximal end of the catheter apparatus for control by a user, e.g. a doctor or clinician.

As another alternative, the actuator may comprise at least two relatively moveable magnetic elements, at least one of the magnetic elements being moveable such that the magnetic poles of the at least two magnetic elements can be brought in and out of alignment.

Preferably, three of the magnetic elements are provided. For example, a first magnet may be located adjacent the first guide wire, e.g. by being embedded in the first section of the tip region, and a second magnet may be located adjacent the second guide wire, e.g. by being embedded in the second section of the tip region. A third magnet may be located between the first and second magnets and may be rotatable between first and second positions. In the first position the north and south poles of the third magnet may be adjacent the south and north poles respectively of the adjacent first and second magnets, whereupon the first and second magnets, and thus the first and second guidewires, will be attracted toward each other. In the second position the north and south poles may be adjacent the north and south poles respectively of the adjacent first and second magnets, whereupon the first and second magnets, and thus the first and second guidewires, will be repelled away from each other.

Preferably, the third magnet element is attached to an elongate control element, e.g. a guidewire, which extends to the proximal end of the catheter apparatus for control by a user, e.g. a doctor or clinician.

As yet another alternative, the actuator may comprise a rotatable cam element. The cam element may be located between the first and second sections, the first and second lumens and/or the first and second guidewires and shaped such that, upon rotation, its diameter across an axis between these first and second elements varies, thus pushing the first and second guidewires apart by varying degrees.

The apparatus may comprise a controller, the controller having an actuation means for moving the actuator, e.g. wedge element, cam element or magnet, relative to the first and/or second lumens to separate their distal end openings. The controller may comprise a housing, and the actuation means may be moveably connected to the housing. The actuation means may comprise a slide button, a rotatable drum, wheel or pusher, for example. The controller housing may comprise a hand grip.

The apparatus may further comprise an introducer, for guiding the guidewires into the lumens. The introducer may be integrated with the controller. The introducer may have a housing having input openings through which the guidewires can be inserted. The housing may comprise tactile features, to enable a person to distinguish by touch one input opening from another.

Optionally, the first guidewire, i.e. the introducer guidewire for guiding the catheter to the CTO, has first and second guidewire sections, the first guidewire section projecting from the distal end of the catheter apparatus and having a spiral shape, and the second guidewire section, connected to the first guidewire section, being located within the first lumen and having a linear shape.

In this application, the term 'spiral shape' is intended to describe a circling, coiling, corkscrewing and/or helical shaped guidewire section. The term 'linear shape' is intended to describe a straight or substantially straight guidewire section.

The spiral shaped first guidewire section can follow a spiral path along the inner walls of a blood vessel in which the catheter is located in order to fix the position of the second guidewire section, and thus the catheter, between the blood vessel walls.

Preferably, the first guidewire section spirals around a central axis which is an extension of the longitudinal axis of the second guidewire section. Accordingly, the first guidewire section may fix the second guidewire section in a central position between the blood vessel walls. By fixing the position of the second guidewire section centrally with respect to the blood vessel walls, variation of the separation between the first and second guidewires, and rotation of the second guidewire about the longitudinal axis of the second guidewire section, will ensure that a circularly symmetrical central area of a calcified cap of a CTO can be probed. Nevertheless, alternatively, the first guidewire section may fix the second guidewire section in a position offset from centre, between the blood vessel walls.

Preferably the first guidewire section is moveable in and out of the first lumen, and is collapsible into a substantially linear shape when positioned and constrained in the first lumen. Preferably, the first guidewire section is arranged to expand automatically into the spiral shape when released from the distal end of the first lumen.

Preferably, the diameter of the spiral shape when in a relaxed, non-constrained state is larger than the diameter of the blood vessel. Accordingly, the first guidewire section may apply a pressure to the blood vessel wall when expanded in order to provide a frictional holding force therebetween. The second guidewire may extend from the distal end of the catheter apparatus through one or more loops of the spiral shape so that it may reach, probe, and traverse the calcified cap of a CTO without obstruction.

According to a third aspect of the present invention, there is provided a catheter apparatus, the catheter apparatus having a proximal end and a distal end, the distal end being for insertion into a patient's body, the apparatus comprising:
  a catheter having a proximal end and a distal end;
  first and second lumens, each lumen comprising a distal opening at the distal end of the catheter apparatus; and
  first and second guidewires accommodated in the first and second lumens respectively, the guidewires being arranged to project from the distal openings of the lumens, wherein
  the first guidewire has first and second guidewire sections, the first guidewire section projecting from the distal opening of the first lumen and having a spiral shape, and the second guidewire section, connected to the first guidewire section, being located within the first lumen and having a linear shape.

The catheter, first and second guidewires and/or first and second lumens in the third aspect may be configured, and serve the same purposes, as the catheter, first and second guidewires and/or first and second lumen described above with respect to the first and second aspects of the invention. For example: preferably the second guidewire is for probing a CTO; preferably the first guidewire section spirals around a central axis which is an extension of the longitudinal axis of the second guidewire section; and preferably, the second guidewire extends from the distal end of the catheter apparatus through one or more loops of the spiral of the first guidewire section so that it may reach, probe, and traverse the calcified cap of a CTO without obstruction.

In any of the above aspects of the invention the catheter apparatus may be provided with a plurality of first lumens and/or a plurality of second lumens. This means that lumens can be selected to accommodate the first and/or second guidewires as desired. The distal openings of all the lumens may effectively be arranged to, in combination, cover the entire surface area of the CTO. Preferably, a plurality of second lumens are provided, each being for accommodating the guidewire for probing a CTO. With this arrangement, rather than rotate the catheter apparatus, so that the second guidewire can be positioned for probing different areas of the CTO, the appropriate second lumen for guiding the guidewire to the desired area of the CTO can be selected. This means that little or no rotation of the catheter may be necessary to probe a large surface area of the CTO.

According to a fourth aspect of the present invention, there is provided a catheter apparatus, the catheter apparatus having a proximal end and a distal end, the distal end being for insertion into a patient's body, the apparatus comprising:
  a catheter having a proximal end and a distal end;
  a guidewire, the guidewire arranged to project from the distal end of the catheter;
  a deflection surface at the distal end of the catheter, and
  an actuator arranged to act between the deflection surface and the guidewire in order to change the separation between the deflection surface and the guidewire at the distal end of the catheter.

The catheter may be inserted into a blood vessel. If the distal end is positioned adjacent a CTO in the blood vessel, by changing the separation between the guidewire and the deflection surface, the guidewire may be used to probe different areas of the calcified cap of a CTO located in a blood vessel in order to find an appropriate pathway, e.g. a microvessel, through the CTO (see discussions above).

The catheter of the fourth aspect of the invention may include any of the features described above with respect to the first, second and third aspects of the invention. For example, the distal end of the catheter may have a tip region comprising first and second sections, the first and second sections being moveable relative to each other, the first section providing the deflection surface and the second section having a lumen which accommodates the guidewire. The first section may have a lumen accommodating a second guidewire for guiding the catheter to the appropriate destination, e.g. a CTO in a blood vessel. The actuator may comprise an inflatable balloon, a wedge element, magnets, electrical means or cam element, configured e.g., as described above.

Preferably, the actuator is an inflatable balloon. The catheter may be a balloon catheter which comprises the expandable balloon. The deflection surface may be provided on an element separate from the balloon catheter, wherein, when the balloon is inflated, the balloon pushes against the deflection surface, causing the distal end of the balloon catheter to deflect, moving the guidewire away from the deflection surface.

Embodiments of the present invention will now be described by way of example only, with reference to the accompanying drawings, in which:

FIG. 2 shows a cross-sectional view of the catheter apparatus of FIG. 1a;

FIGS. 6a and 6c show cross-sectional views of catheter apparatus according to a fourth embodiment of the present invention in a normal and expanded state respectively;

FIGS. 6b and 6d show cross-sectional views along the planes indicated by dotted lines B-B and D-D in FIGS. 6a and 6c respectively.

FIG. 11a shows an end view, and FIG. 11b shows a cross-sectional side view, of a catheter apparatus according to a seventh embodiment of the present invention;

FIG. 12a shows an end view, and FIG. 12b shows a cross-sectional side view, of the catheter apparatus of FIGS. 11a and 11b with distal end openings of lumens moved apart by a wedge element;

FIG. 17a shows a side view of a first example of a guidewire introducer, attached to the catheter of catheter apparatus of FIGS. 11a and 11b, and FIG. 17b shows and end view, and FIG. 17c shows a cross-sectional view of the guidewire introducer;

FIGS. 18a and 18b show a side view and end view respectively of a second example of a guidewire introducer;

FIGS. 19a and 19b show an oblique view and a side view respectively of a third example of a guidewire introducer;

FIG. 24 shows a cross-sectional side view of the controller of FIGS. 23a to 23e;

FIG. 25 shows an oblique transparent view of the controller of FIGS. 23a to 23e; and FIGS. 26a and 26b show the movement of the actuation mechanism of the controller of FIGS. 23a to 23e.

Figure 1A:
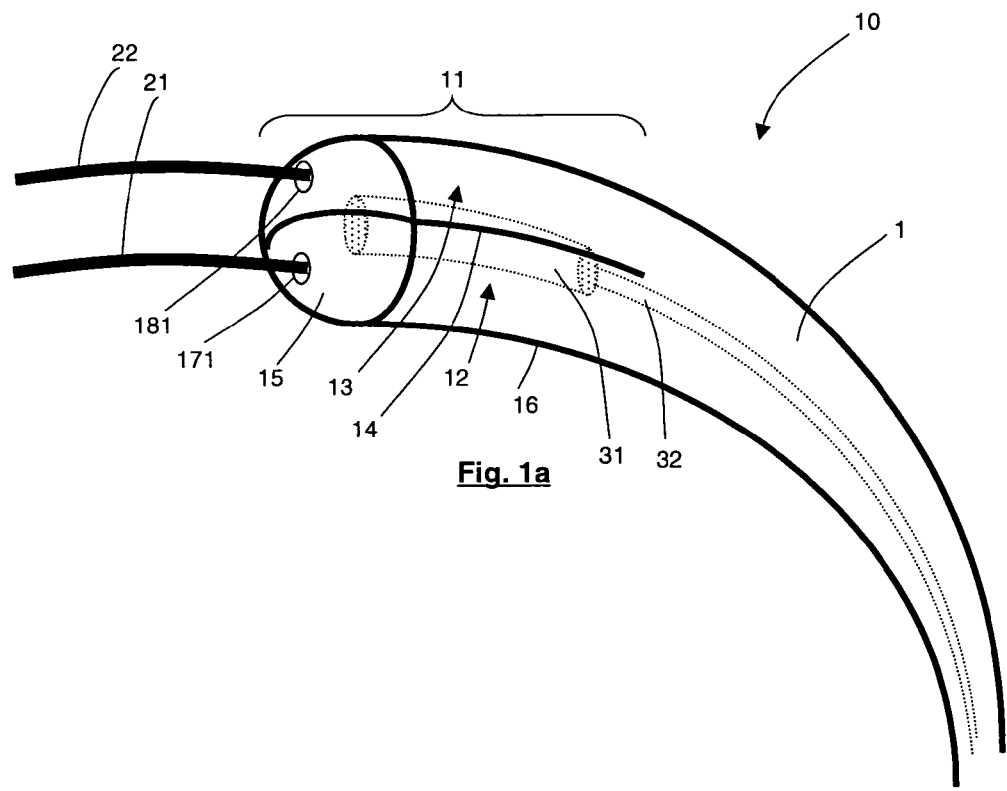
FIGS. 1a and 1b show oblique views of a catheter apparatus according to a first embodiment of the present invention in a normal and expanded state respectively.

In FIGS. 1a, 1b, 2 and 3, a catheter apparatus 10 according to a first embodiment of the present invention is shown, which comprises a catheter 1, having a tip region 11. The tip region 11 is located at the distal end of the catheter and comprises first and second sections 12, 13 which are relatively moveable. The first and second sections 12, 13 are formed by a split 14, which extends across a distal end face 15 of the catheter 1 and along opposing sides of the catheter walls 16, dividing the tip region 11 into the two sections 12, 13. The catheter 1 has a cross-section which is substantially circular, and the first and second sections 12, 13 have cross-sections which are substantially semi-circular, in a direction perpendicular to the longitudinal direction of the catheter 1.

The first and second sections 12, 13 comprise first and second lumens 17, 18 respectively (see FIG. 2), the lumens extending from the proximal end (not shown) of the catheter 1 to distal openings 171, 181 on the distal end face 15 of the catheter. The first and second lumens 17, 18 are arranged to accommodate first and second guidewires 21, 22 respectively. In the Figures, the guidewires 21, 22 are shown projecting from the distal openings 171, 181 of the lumens 17, 18.

The first guidewire 21 is provided to guide the catheter 1 to a desired region of a blood vessel, adjacent a chronic total occlusion (CTO). The second guidewire 22 is provided to probe the CTO, to find a pathway therethrough. In this embodiment, the guidewires 21, 22 have 0.014" (0.36 mm) diameters.

Figure 1B:
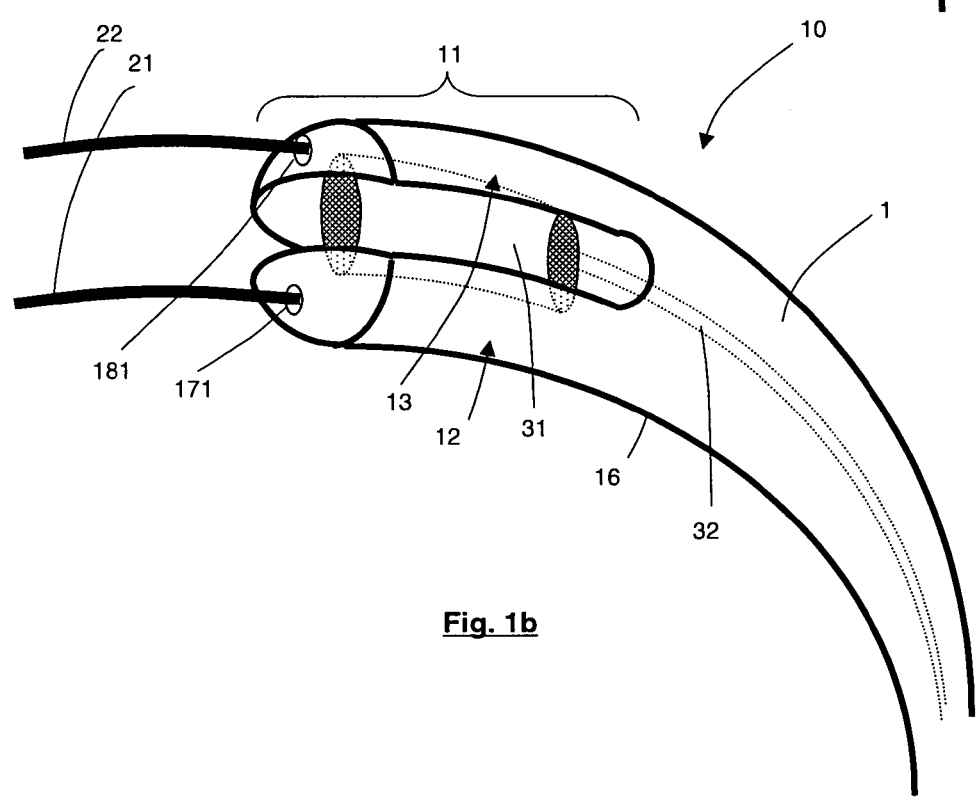
Figure 2:
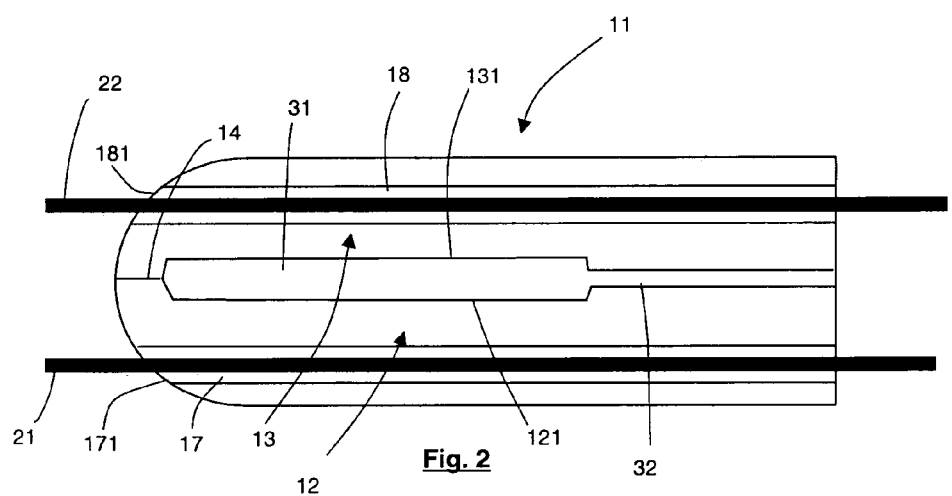
Figure 3:
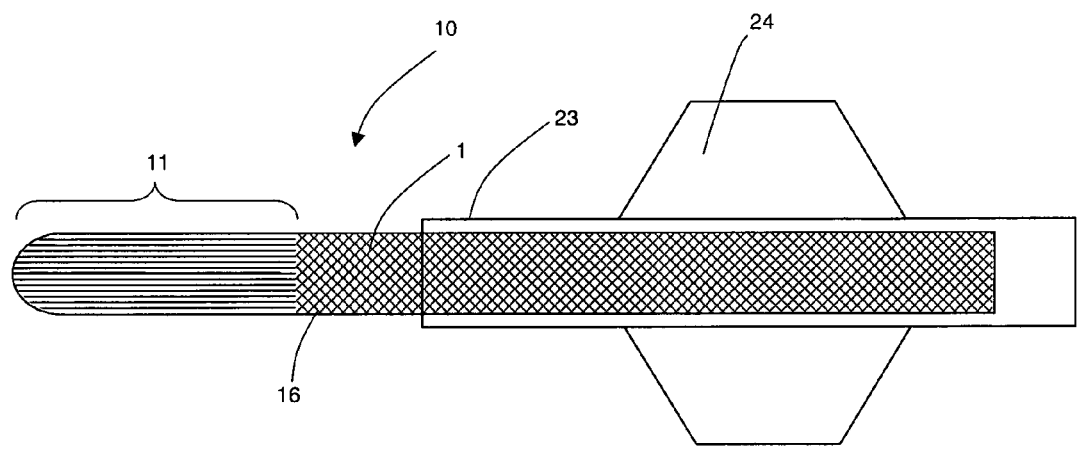
FIG. 3 shows a side view of the catheter apparatus of FIG. 1a with a delivery sleeve

The first and second sections 12, 13 are separable using an inflatable balloon 31 provided within the catheter 1. The inflatable balloon 31 is located between opposing inner walls 121, 131 of the first and second sections 12, 13 respectively and is arranged, upon inflation, to press against the inner walls 121, 131 in order to push the first and second sections 12, 13 apart, as shown in FIG. 1b. The inflatable balloon 31 is connected to a tube 32, which extends to the proximal end of the catheter 1 where fluid (preferably liquid) can be pumped into the tube 32 to inflate the balloon 31. The degree of separation between the first and second sections 12, 13 can be controlled by controlling the degree of inflation of the inflatable balloon 31. Although in this embodiment the inner walls 121, 131 remain substantially parallel as they are moved apart, the angle of the inner walls 121, 131 may be arranged to change relative to each other upon inflation of the balloon 31, e.g. diverge toward the distal end face 15 of the catheter 1, in order to changing the angle of the second guidewire 22 projecting from the respective distal opening 181.

Since the first and second sections 12, 13 can be moved apart, the position of the second lumen 18, which comprises the second (probe) guidewire 22, can be adjusted relative to the CTO and thus the second guidewire 22 can probe different positions of the calcified cap of the CTO in order to find an appropriate pathway, such as a microvessel, through the CTO.

Once through, a larger guidewire may be inserted through the pathway to widen the pathway such that a balloon catheter can be inserted through the CTO. The inserted balloon can then be inflated, crushing the calcification and plaque of the CTO against the vessel wall. A stent can then be inserted into the open vessel and expanded to ensure the vessel remains open.

To enable a greater area of the calcified cap of the CTO to be probed by the second guidewire 22, the catheter apparatus is arranged to be rotatable. In this embodiment, the catheter 1 is arranged to be rotatable within an introducer shaft 23 (see FIG. 3), which is a stiff hollow sleeve member through which the catheter 1 extends. To allow stable rotation of the catheter 1, the introducer shaft 23 comprises an inflatable balloon 24 for anchoring the shaft 23 against the walls of the blood vessel adjacent the CTO. As indicated by the patterning in FIG. 3, the walls 16 of the catheter 1 have braiding to provide reinforcement, the braiding being different at the tip region 11 of the catheter 1 to the rest of the catheter to permit the separation of the first and second sections 12, 13.

Although, in this embodiment, the catheter 1 is rotated within the introducer shaft 23, the catheter 1 may alternatively be rotated about the longitudinal axis of the first guidewire 21.

To control rotation, the proximal end (not shown) of the catheter 1 may be manipulated by hand.

Since the second guidewire 22 can be moved in a linear direction, by changing the separation of the first and second sections 12, 13, and in a rotational direction, by rotating of the catheter 1, a substantially circular or annular area of the calcified cap of the CTO may be swept out and probed by the second guidewire 22. Having a larger probe area means that versatility of the catheter apparatus is enhanced; it is more likely that the guidewire 22 can be manipulated to probe and travel through an appropriate pathway of the CTO.

Figure 4A:
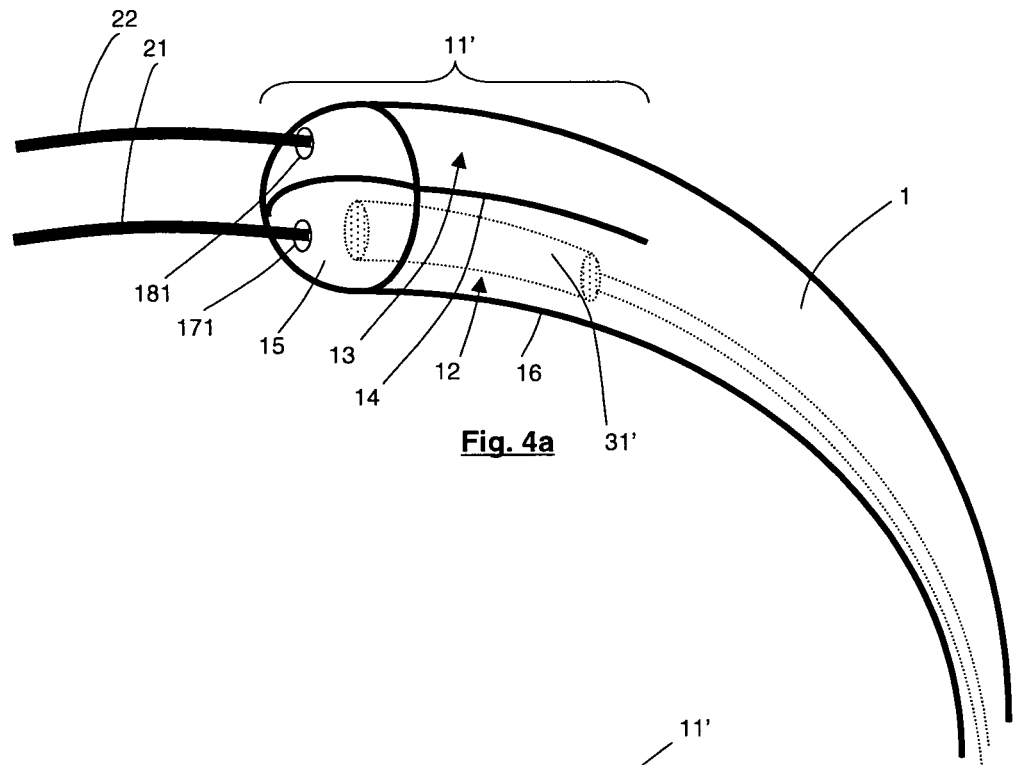
FIGS. 4a and 4b show an oblique view and a cross-sectional view respectively of a catheter apparatus according to a second embodiment of the present invention.
Figure 4B:
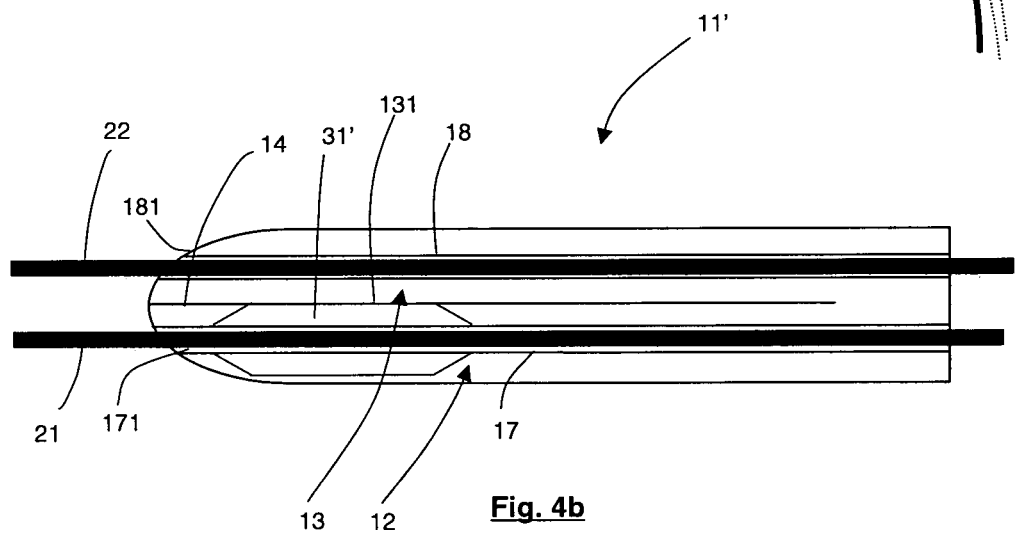

In FIGS. 4a and 4b, a tip region 11' of a catheter apparatus according to a second embodiment of the present invention is shown. The catheter apparatus of the second embodiment has generally the same features and works under generally the same principles as the catheter apparatus 10 according to the first embodiment, except that the inflatable balloon 31' is positioned to surround a section of the first lumen 17. Effectively, a standard balloon catheter may be used to provide the first lumen 17 and balloon 31'.

The inflatable balloon 31 is located within a cavity in the first section 12. The cavity has an opening adjacent the inner wall 131 of the second section 13 such that, upon inflation, the balloon can press against the inner wall 131 to separate the first and second sections 12, 13.

Since the balloon surrounds a section of the first lumen 17, the tip region 11' can take a substantially lower profile, and may therefore extend along narrower blood vessels.

Figure 5A:
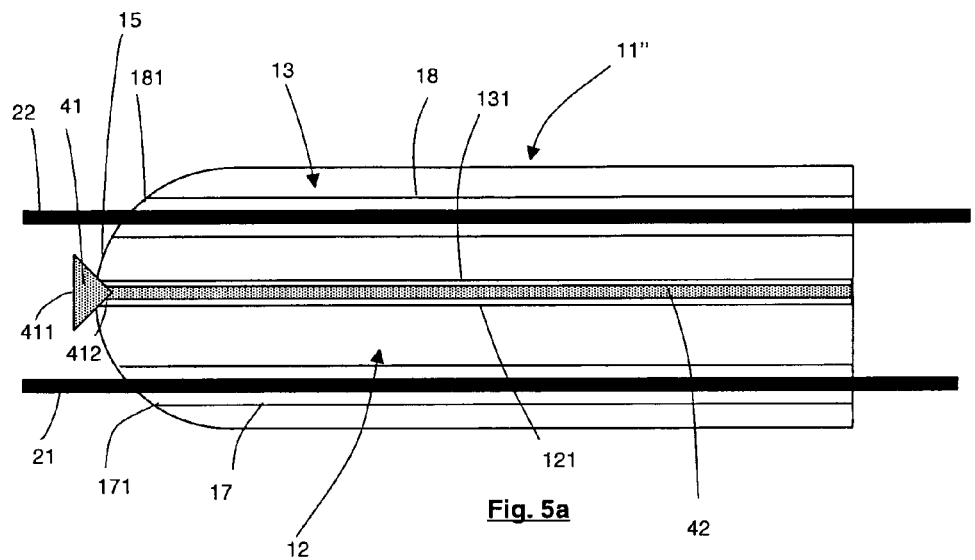
FIGS. 5a and 5b show cross-sectional side views of a catheter apparatus according to a third embodiment of the present invention in a normal and expanded state respectively.
Figure 5B:
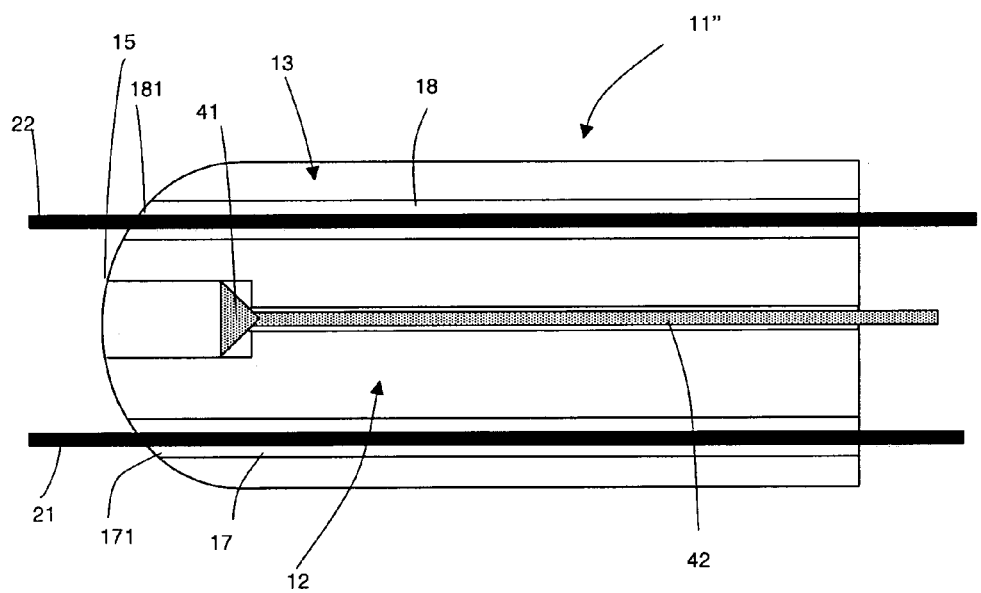

In FIGS. 5a and 5b, a tip region 11" of a catheter apparatus according to a third embodiment of the present invention is shown. The catheter apparatus of the third embodiment has generally the same features and works under generally the same principles as the catheter apparatuses according to the first and second embodiments, except that a wedge element 41 is provided to separate the first and second sections 12, 13 at the tip region 11" of the catheter 1, rather than an inflatable balloon 31, 31'. Features of the third embodiment corresponding to features of the first and second embodiments are given the same reference numerals, and will not be described again.

The wedge element 41 is connected to an elongate control element 42, which extends to the proximal end of the catheter 1, for control by e.g., a doctor or clinician. As seen in cross section, the wedge element 41 is thick at a distal end 411 and tapers to a point at a proximal end 412.

By pulling the elongate control element 42, the wedge element 41 can be moved from a first position as shown in FIG. 4a, where it is located proximate the distal end face 15 of the catheter 1, to a second position in which it is fully located between the inner walls 121, 131 of the first and second sections 12, 13 as shown in FIG. 4b. The wedge element 41 forces the first and second sections 12, 13 apart as it moves from the first position to the second position. The elongate control element 42 is stiff so that it can also be pushed in order to move the wedge element 41 back to the first position. The position of the wedge element 41 can be varied between the first and second positions to change the separation of the first and second sections 12, 13 to the desired degree.

In FIGS. 6a to 6d, a tip region 11'" of a catheter apparatus according to a fourth embodiment of the present invention is shown. The catheter apparatus of the fourth embodiment has generally the same features and works under generally the same principles as the catheter apparatuses according to the previous embodiments, except that a cam element 51 is provided to separate the first and second sections 12, 13 at the tip region 11'" of the catheter 1, rather than an inflatable balloon 31, 31' or a wedge element 41. Features of the third embodiment corresponding to features of the first and second embodiments are given the same reference numerals, and are not described again.

The cam element 51 is connected to an elongate control element 52, which extends to the proximal end of the catheter 1, for control by e.g., a doctor or clinician. In this embodiment, the cam element 51 is a plate shaped element with first opposing parallel surfaces 53a, 53b and second opposing parallel surfaces 54a, 54b, the first opposing surfaces 53a, 53b having smaller separation than the second opposing surfaces 54a, 54b.

By rotating the elongate control element 52, the cam element 51 can be rotated about an axis substantially parallel to the longitudinal direction of the catheter 1 from a first position as shown in FIGS. 6a and 6b, where its first opposing surfaces 53a, 53b abut the inner walls 121, 131 of the first and second sections 12, 13, to a second position in which its second opposing surfaces 54a, 54b, which are spaced further apart than the first opposing surfaces, abut the inner walls 121, 131 of the first and second sections 12, 13 as shown in FIGS. 6c and 6d. The cam element 51 forces the first and second sections apart as it rotates from the first position to the second position. The elongate control element 52 can be rotated in either direction, or rotated 360 degrees, so that the cam element 51 can be moved back to the first position from the second position. The position of the cam element 51 can be varied between the first and second positions to change the separation of the first and second sections 12, 13 to the desired degree.

Figure 7B:
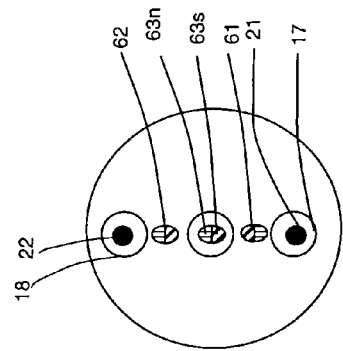
FIGS. 7b and 7d show cross-sectional views along the planes indicated by dotted lines B-B and D-D in FIGS. 7a and 7c respectively.
Figure 7D:
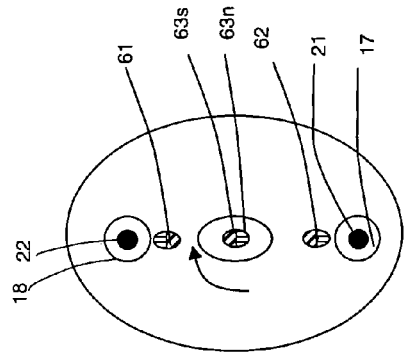
Figure 7A:
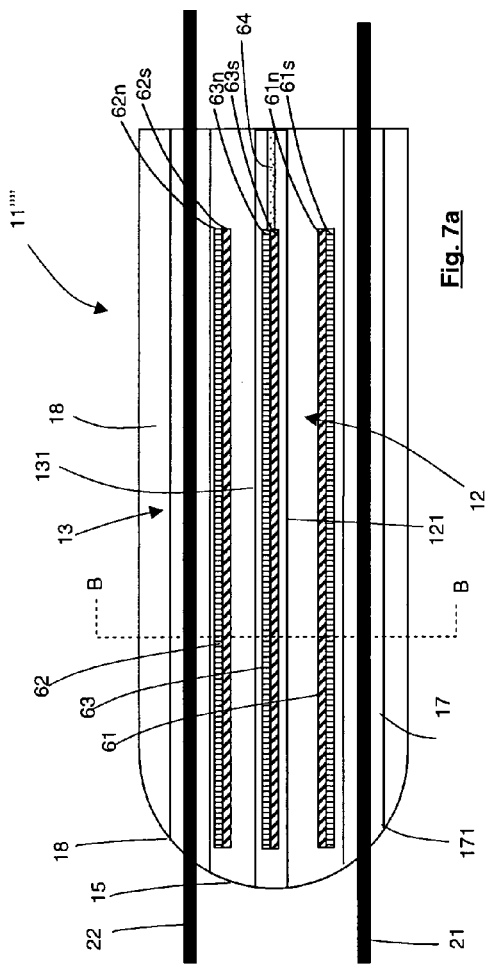
FIGS. 7a and 7c show cross-sectional views of catheter apparatus according to a fifth embodiment of the present invention in a normal and expanded state respectively.

In FIGS. 7a and 7b, a tip region 11"" of a catheter apparatus according to a fifth embodiment of the present invention is shown. The catheter apparatus of the fifth embodiment has generally the same features and works under generally the same principles as the catheter apparatuses according to the previous embodiments, except that magnets 61, 62, 63 are provided to separate the first and second sections 12, 13 at the tip region 11"" of the catheter 1, rather than an inflatable balloon 31, 31', wedge element 41 or cam element 51. Features of the fifth embodiment corresponding to features of the previous embodiments are given the same reference numerals, and will not be described again.

A first magnet 61 is embedded in the first section 12, adjacent the inner wall 121; a second magnet 62 is embedded in the second section 13, adjacent the inner wall 131, and a third magnet 63 is located between the first and second sections 12, 13.

In this embodiment, the magnets 61, 62 or 63 are permanent magnets, although they could be, alternatively, electromagnets or a combination of permanent magnets and electromagnets.

Each magnet 61, 62, 63 has a north pole and a south pole. In this embodiment, the north pole 61n of the first magnet 61 is adjacent the inner wall 121 of the first section 12, and the south pole 62s of the second magnet 62 is adjacent the inner wall 131 of the second section 13. The third magnet is connected to an elongate control element 64, which extends from the third magnet 63 to the proximal end of the catheter 1, for control by e.g., a doctor or clinician.

Figure 7C:
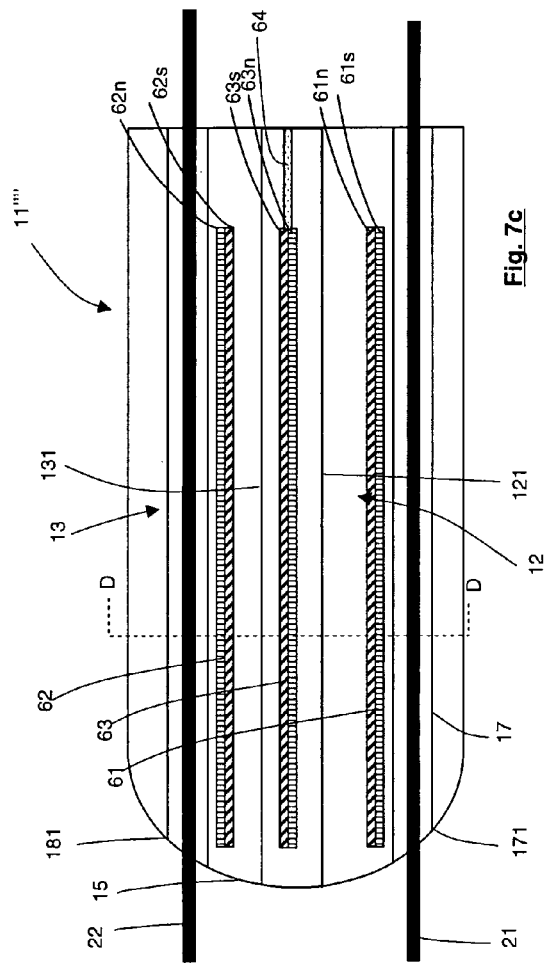

By rotating the elongate control element 62, the third magnet 63 can be rotated about an axis substantially parallel to the longitudinal direction of the catheter 1 from a first position to a second position. In the first position, as shown in FIGS. 7a and 7b, the south pole 63s of the third magnet 62 is adjacent the north pole 61 n of the first magnet 61, and the north pole 63n of the third magnet 63 is adjacent the south pole 62s of the second magnet 62. In the second position, as shown in FIGS. 7c and 7d, the north pole 63n of the third magnet 62 is adjacent the north pole 61n of the first magnet 61, and the south pole 63s of the third magnet 63 is adjacent the south pole 62s of the second magnet 62. The arrangement is such that: in the first position, the first and second magnet 61, 62 and thus the first and second sections 12, 13 are attracted toward the third magnet and are therefore closer together or touching; and in the second position, the first and second magnets 61, 62 and thus the first and second sections 12, 13, are repelled from the third magnet and are therefore further apart.

The position of the magnet element 63 can be varied between the first and second positions to change the separation of the first and second sections 12, 13 to the desired degree.

If electromagnets are used, rather than rotating the third magnet to change the positions of its north and south poles, the third magnet can be kept stationary, and the polarity of the power supply to the third magnet, or the polarity of power supplies to the first and second magnet can be switched to change between the attractive and repulsive states discussed above. Furthermore, to vary the degree of separation of the first and second sections 12, 13, the strength of the power supply can be adjusted.

Figure 8A:
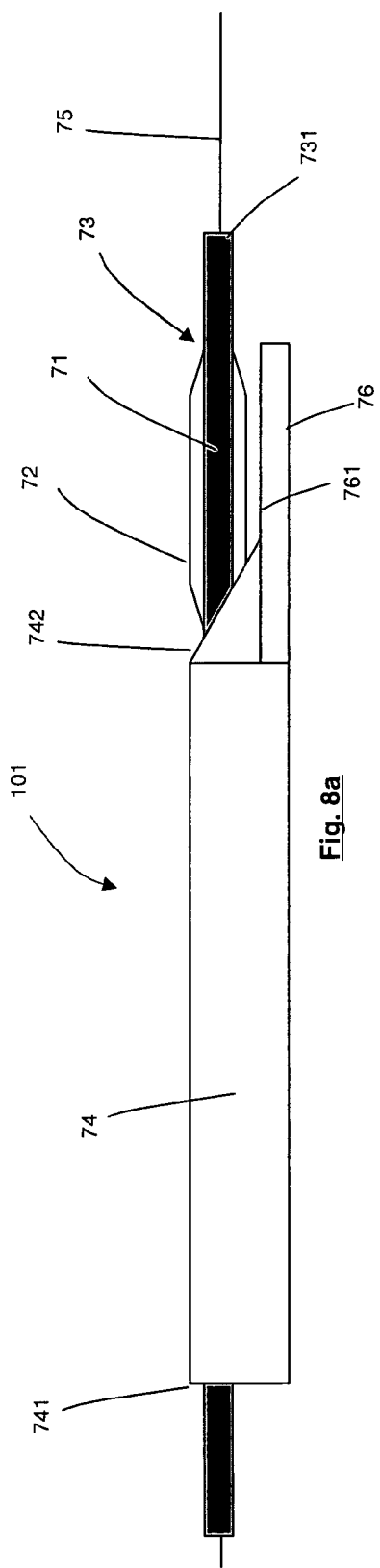
FIGS. 8a and 8b show side views of catheter apparatus according to a sixth embodiment of the present invention in a deflected and non-deflected state respectively.
Figure 8B:
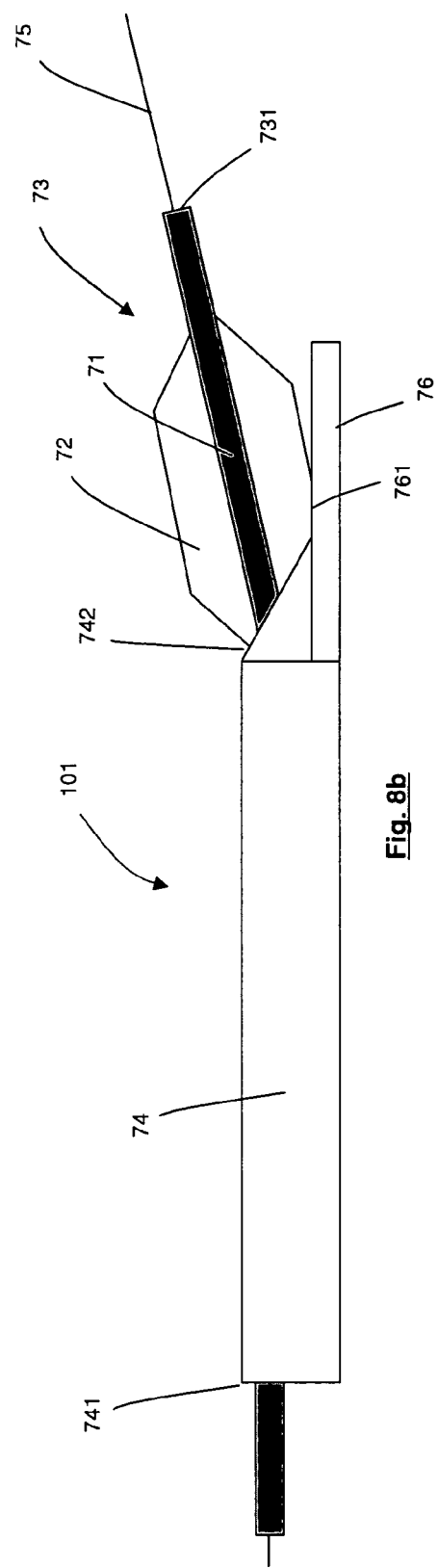

In FIGS. 8a and 8b, a catheter apparatus 101 according to a sixth embodiment of the present invention is shown. The apparatus comprises a balloon catheter 71 that has an inflatable balloon 72 adjacent a tip region 73 at the distal end of the catheter 71. The balloon catheter extends through a sleeve member 74 having a proximal opening 741 and a distal opening 742. The sleeve member 74 can be inserted into the blood vessel along with the balloon catheter 71. A guidewire 75 extends through the balloon catheter 71 and projects from a distal opening 731 at the tip region 73 of the balloon catheter 71.

A projecting part 76 extends from the sleeve member 74 at its distal opening 742. The projecting part 76 has a deflection surface 761 that runs alongside the tip region 73 of the balloon catheter 71, adjacent the inflatable balloon 72. As seen in FIG. 8a, when the balloon 72 is deflated it makes no contact with the deflection surface 761. However, upon inflation the balloon 72 is arranged to press against the deflection surface 761, causing the tip region 73 of the balloon catheter 71 to deflect away from the deflection surface 761.

The sleeve member may be held in position, e.g. by an anchoring member (not shown) in a blood vessel adjacent a CTO. By inflating and deflating the balloon 72, the tip region 73 of the catheter 71, and thus the guidewire 75 projecting therefrom, will move relative to the deflection surface 761 and therefore the CTO. Accordingly, the guidewire 75 can probe different positions of the calcified cap of the CTO in order to find an appropriate pathway, such as a microvessel, through the CTO. As in the embodiments described above, the catheter apparatus may be rotatable so that the guidewire may probe a substantially circular or annular area of the cap of the CTO.

Figure 9A:
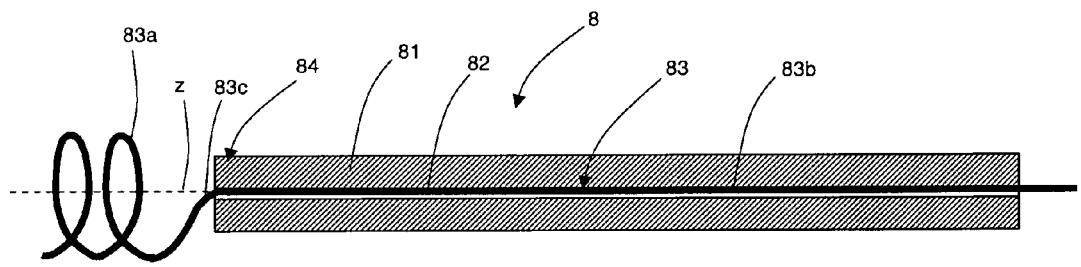
FIGS. 9a and 9b show a side view and an end view respectively of a catheter and a guidewire with a spiral shaped distal end.
Figure 9B:
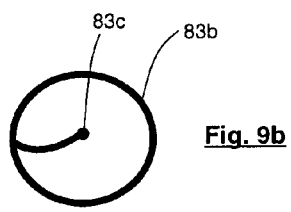
Figure 9C:
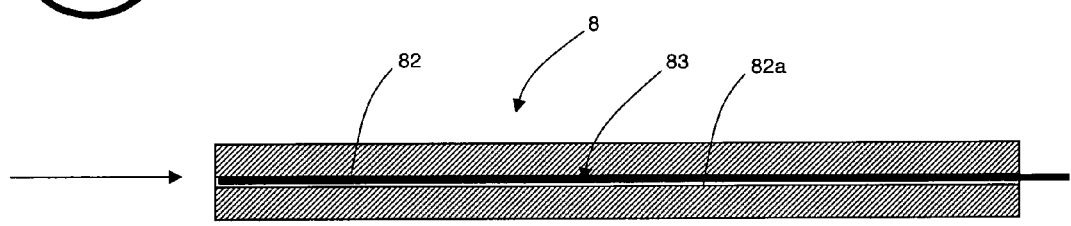
FIG. 9c shows a cross-sectional view of the catheter of FIG. 9a with the distal end retracted into the catheter.

FIGS. 9a to 9c shows a catheter apparatus comprising a catheter 81 which has a lumen 82 through which a guidewire 83 extends. A first guidewire section 83a of the guidewire 83 projects from the distal end of the catheter 81 and has a spiral shape. The first guidewire section 83a is connected to a second guidewire section 83b of the first guidewire 83 that is substantially linear, and which is located within the lumen 82. As can be seen from the distal end view of the guidewire 83 in FIG. 9b, the spiral shaped first guidewire section 83a has a substantially circular perimeter, and is joined to the linear second guidewire section 83a at a position 83c at the centre of the circle. Essentially, the first guidewire section 83a spirals around a central axis (indicated by line z in FIG. 9a) which is an extension of the longitudinal axis of the second guidewire section 83b.

The first section 83a can be slid in and out of the lumen 82. When located in the lumen as shown in FIG. 9c, the first section 83a is forced to collapse and take a linear shape, as the second section 83b.

Figure 10:
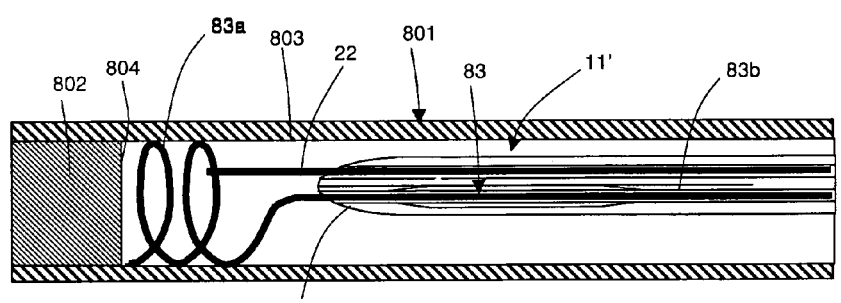
FIG. 10 shows a cross-sectional side view of a catheter apparatus as shown in FIG. 2 used with guidewire with a spiral shaped distal end as shown in FIGS. 9a to 9c.
Figure 13A:
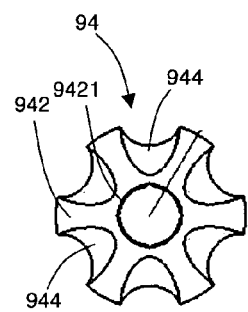
FIGS. 13a and 13b show distal and proximal end views of the wedge of FIGS. 11a to 12b.
Figure 13B:
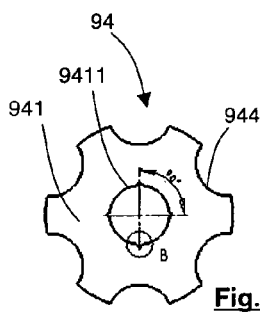
Figure 13D:
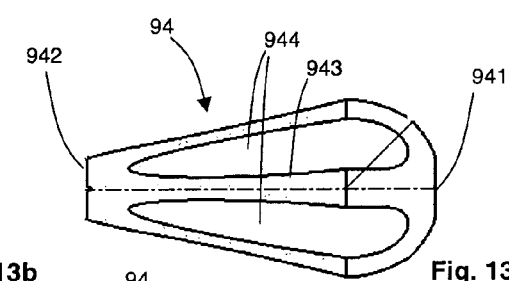
FIG. 13d shows a side view of the wedge.
Figure 13C:
FIG. 13c shows a close-up view of area B in FIG. 13b.
Figure 13F:
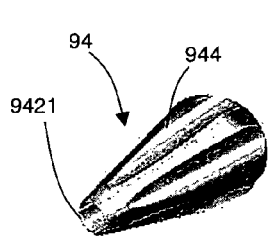
FIGS. 13f and 13g show oblique views of the wedge.
Figure 13G:
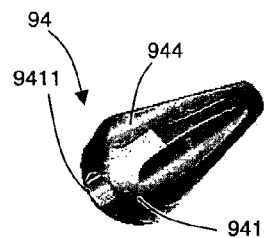
Figure 13E:
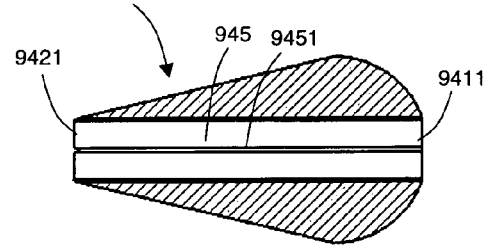
FIG. 13e shows a cross-section side view of the wedge.

FIG. 10 shows a tip region 11' of a catheter apparatus as described above with respect to the second embodiment of the present invention. The tip region 11' is located in a blood vessel 801, adjacent a CTO 802. A guidewire 83, as described above with respect to FIGS. 9a to 9c, is disposed in the first lumen 17 of the catheter. The spiral shaped first section 83a of the guidewire extends from the distal end of the catheter and abuts the blood vessel walls 803.

Since the first guidewire section 83a spirals around a central axis which is an extension of the longitudinal axis of the second guidewire section 83b, the second guidewire section 83b is fixed in a central position between the blood vessel walls. By fixing the position of the second guidewire section 83b centrally with respect to the blood vessel walls, variation of the separation between the first and second guidewires 83, 22, and rotation of the second guidewire 22 about the longitudinal axis of the second guidewire section 83b, will ensure that a circularly symmetrical central area of a calcified cap 804 of the CTO 802 can be probed.

In FIGS. 11 a to 12b, the tip region 91 of a catheter apparatus 9 according to a seventh embodiment of the present invention is shown. In this embodiment, the catheter apparatus 9 includes a catheter 92 comprising seven lumens. Each lumen is provided by a respective tube 921, 931 that extends in the elongation direction of the catheter 92 between the distal and proximal ends 901, 902 of the catheter 92. A distal opening 922, 932 of each of the lumens is provided at the distal end 901 of the catheter 92.

As shown in FIG. 11 a, the distal openings 932 of six of the seven lumens (outer lumens) are arranged in a circular formation around the distal opening 922 of the other of the seven lumens (central lumen).

With reference to FIGS. 11b, 12b and 14a to 14c, along most of the length of the catheter 9, between its distal and proximal ends 901, 902, the outer tubes 931 providing the outer lumens are attached to one another, directly or indirectly. However, at the tip region 91 of the catheter 92, proximate the distal end 901, the outer tubes 931 are not attached to one another, and are therefore moveable relative to each other and to the central tube 921, at the tip region 91.

The catheter apparatus comprises a wedge element 94 that is operable to separate the distal ends 922, 932 of the lumens at the tip region 91. The central tube 921, providing the central lumen, is fixed to the wedge element 94 to provide an elongate control element, which extends to the proximal end 902 of the catheter 92, for control of the wedge element 94 by e.g., a doctor or clinician. The central tube 921 and the outer tubes 931 are relatively moveable in the elongation direction of the catheter 92.

With reference to FIGS. 13a to 13g, the wedge element 94 is substantially conical, with side surfaces 943 extending between a distal end surface 941 and a proximal end surface 942. The diameter of the wedge element 94 tapers from the distal end surface 941 to the proximal end surface 942. The side surfaces 943 are provided with a plurality of channels 944 for guiding the outer tubes 931 of the catheter 92. The wedge element 94 has a central conduit 945, extending between distal and proximal end openings 9411, 9421, into which the central tube 931 is located. Effectively, the distal end opening 9411 of the conduit 945 provides the distal opening 922 of the central lumen. In this embodiment, the central tube 921 is fixed to inner surface of the central conduit 945 by glue. To direct the glue between the inner surface of the central conduit 945 and the central tube 921, a plurality of wicking channels 9451 are provided along the inner surface.

Figure 14A:
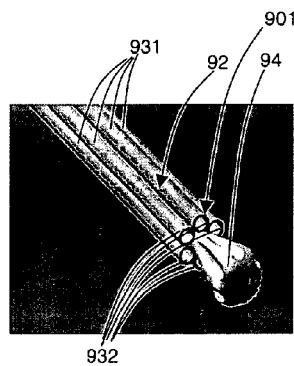
FIGS. 14a to 14c show perspective views.
Figure 14B:
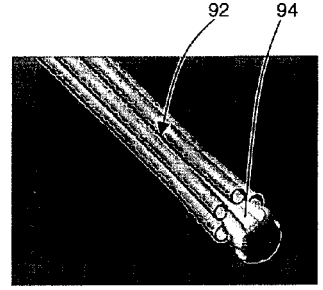
Figure 14C:
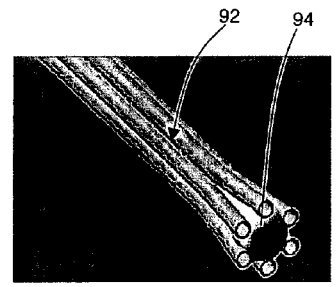
Figure 15A:
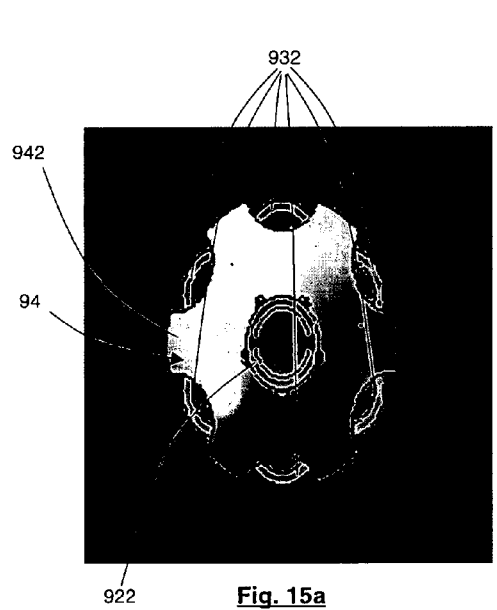
FIGS. 15a and 15b show end views, of the wedge separating the distal end openings of the catheter apparatus of FIGS. 11a and 11b.
Figure 15B:
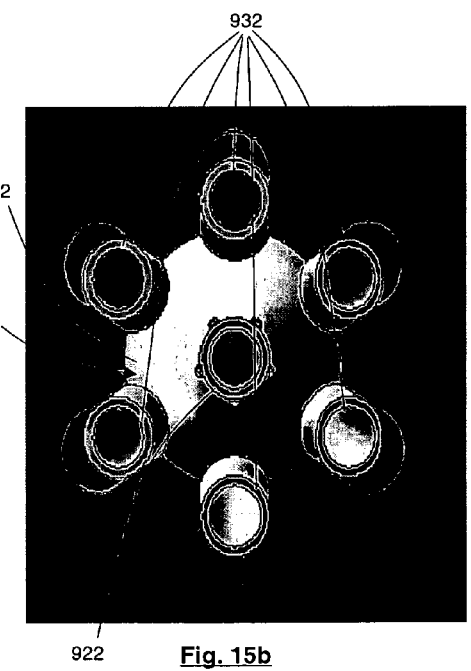

As indicated above, the central tube 921 acts as an elongate control element for the wedge element 94 (although in alternative embodiments, a control element separate from the central tube 921 may be provided). Since the central tube 921 is moveable relative to the outer tubes 931, the wedge element 94 is also moveable relative to the outer tubes 931. By relatively moving the wedge element 94 and the outer tubes 931, the wedge element 94 can be moved from a first position as shown in FIGS. 11b, 14a and 15a, where it is positioned outside the catheter 92, at the distal end 901 of the catheter 92, to a second position as shown in FIGS. 12b and 14c and 15b, where it is located between the outer tubes 931 at the tip region 91 of the catheter 92. As it moves from the first position to the second position, the wedge element 94 forces the outer tubes 931 apart, and thus the distal openings 932 of the outer lumens apart. Relative movement of the wedge element 94 and the outer tubes 931 can be achieved by, for example, moving the wedge element 94, whilst keeping the outer tubes 931 generally stationary, or by moving the outer tubes 931 and keeping the wedge element 94 generally stationary. The central tube 921 and/or outer tubes 931 are stiff so that they can be pushed and pulled in order to relatively move the wedge element 94 between the first and second positions. The position of the wedge element 94 can be varied between the first and second positions (e.g. to an intermediate position as shown in FIG. 14b) to change the separation of the distal end openings 922, 932 to the desired degree. It should be noted that the distal end opening 922 of the central lumen is not shown in FIGS. 14a to 14b.

In this embodiment, the central lumen provided by the central tube 921 is intended to provide a path for a first guidewire, which guidewire is for guiding the catheter 92 to a desired region of a blood vessel, adjacent a chronic total occlusion (CTO). The outer lumens provided by the outer tubes 931 are intended to provide a plurality of selectable paths for a second guidewire that is to probe the CTO, to find a pathway therethrough. Nevertheless, it is conceived that the first guidewire could be extended through one of the outer lumens, leaving the central lumen available to provide one of the plurality of selectable paths for the second guidewire, along with the remaining outer lumens.

Figure 16A:
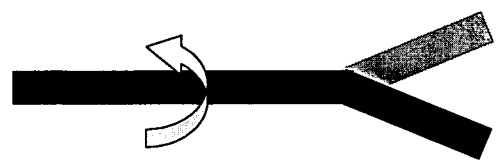
FIG. 16a shows a guidewire with a bent tip, for probing a CTO.
Figure 16B:
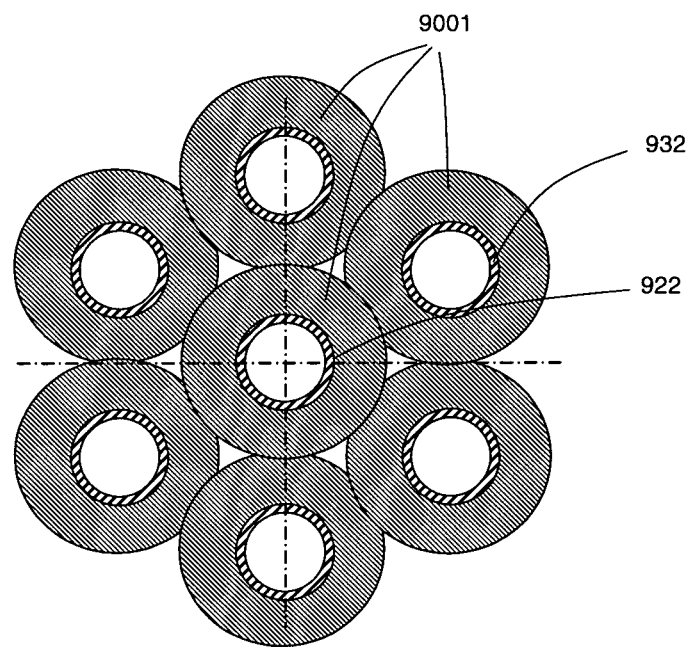
FIG. 16b shows the area that the bent tip can be moved when the guidewire extends from the distal end openings of the catheter apparatus of FIGS. 11a and 11b.

By making the distal openings 922, 932 of the lumens separable at the tip region 91 of the catheter 92, the distal openings 932 of the outer lumens can each be moved along different linear paths, the paths extending radially from the distal opening 922 of the central lumen. By having the plurality of outer lumens, the second guidewire can be moved from one outer lumen to another, and therefore along the different linear paths upon actuation of the wedge element 94, in order to probe different areas of the CTO. This means that little or no rotation of the catheter apparatus 9 may be necessary to probe a relatively large surface area of the CTO. In essence, instead of rotating the catheter apparatus 9 to probe a larger area of the CTO, as described with respect to earlier embodiments, the second guidewire can be moved from one outer lumen to another. The second guidewires may have bent and/or bendable distal ends, as represented in FIG. 16a. Accordingly, whilst projecting out of the distal end openings 922, 932 of the lumens, the distal ends of the second guidewire can be bent and/or rotated to probe a greater area of the CTO. The area that such a guidewire can probe using the apparatus of this embodiment is is represent by the circles 9001 in FIG. 16b.

With reference to FIGS. 17a to 17c, at the proximal end 902 of the catheter 92, a guidewire introducer 95 is provided to assist in locating the guidewires in the central and outer tubes 921, 931. The guidewire introducer 95 comprises a housing having a cylindrical section 951 and a conical section 952 and a plurality of conduits 953 extending through the cylindrical and conical sections 951, 952, each conduit 953 being adapted to channel a guidewire into a respective one of the outer and central lumens of the catheter 92. The conduits 953 have input openings 955 located at a proximal end face 954 of the housing. The conduits 953 increase in diameter toward their input openings 955, to enable easier introduction of a guidewire into the conduits 953. The conduits 953 extend from their input openings 955, through the cylindrical section 951 and into the conical section 952 of the housing, where they converge (not shown). The outer and central lumens of the catheter 92 are each connected to a respective conduit 953 at the distal end 9521 of the conical section 952.

The introducer 95 may comprise tactile features, to enable a person to distinguish by touch one input opening 955 from another. In one embodiment, shown in FIGS. 18a and 18b, the tactile features are provided by a plurality of steps 956 forming the proximal end face 954' of the housing, each input opening 955 being located on a different one of the steps 956. The arrangement of steps 956 may provide a 'spiral staircase' arrangement to the proximal end face 945' of the housing. In another embodiment, shown in FIGS. 19a and 19b, outer surfaces of the housing are provided with a plurality of protrusions 957. The protrusions 957 are clustered together in lines (although alternative arrangements are possible) adjacent each input opening, the number of protrusions 957 in each cluster being distinct to the adjacent input opening 955. Although not shown, it is also conceived that the tactile features might be provided by grooves or depressions in the housing.

Figure 20:
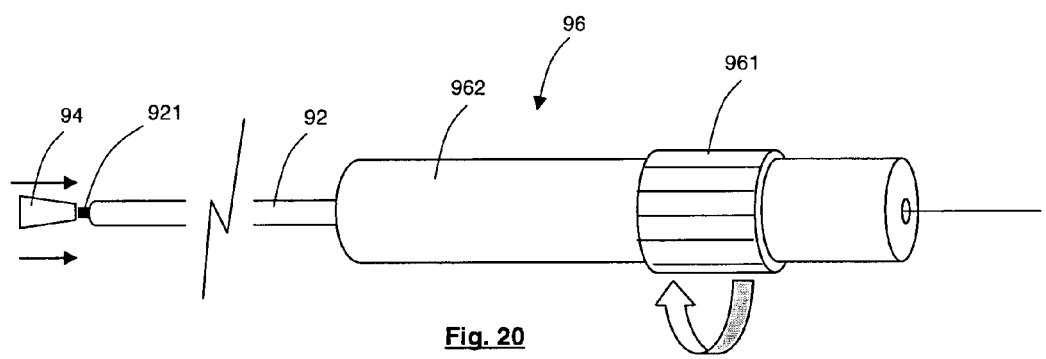
FIG. 20 shows a first example of a controller for controlling movement of the wedge element of the catheter apparatus of FIGS. 11a and 11b.
Figure 21:
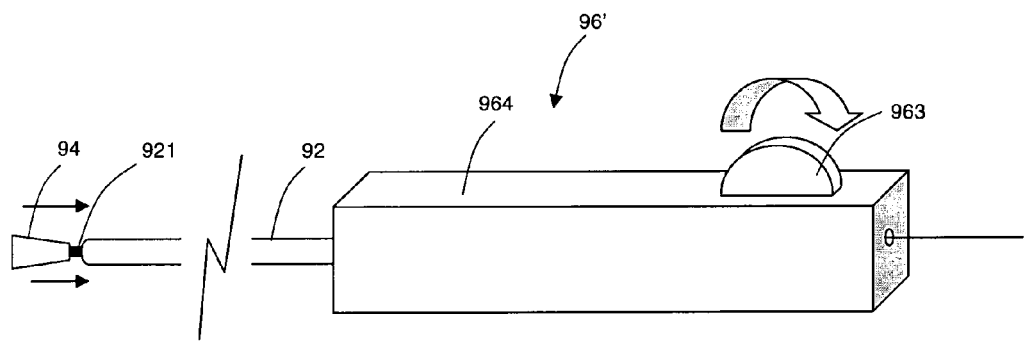
FIG. 21 shows a second example of a controller for controlling movement of the wedge element of the catheter apparatus of FIGS. 11a and 11b.
Figure 22:
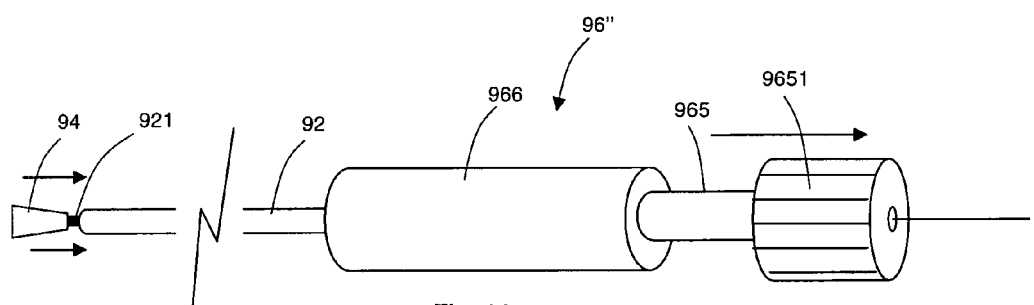
FIG. 22 shows a third example of a controller for controlling movement of the wedge element of the catheter apparatus of FIGS. 11a and 11b.

To control the movement of the wedge element 94 relative to the outer tubes 931, a controller is also provided at the proximal end 902 of the catheter. The controller comprises a housing supporting an actuator element that, e.g. via a rotational to linear force translator and/or gearing etc., is connected to the central tube 921, or connected to the outer tubes 931, in order to control relative movement of the wedge element 94 and the outer tubes 931. The actuator element is moveable relative to the housing to control the relative movement. In one embodiment (see FIG. 20), the actuator element of the controller 96 is a drum 961. The drum 961 is rotatable around the housing 962 and about the axis of elongation of the control element. In another embodiment (see FIG. 21), the actuator element of the controller 96' is a wheel 963. The wheel 963 is rotatable in a slot in the housing 964 and about an axis perpendicular to the axis of elongation of the control element. In yet another embodiment (see FIG. 22), the actuator element of the controller 96" is a push element 965 with a handle 9651. The push element 965 is moveable in and out of the housing 966 along the axis of elongation of the control element, and is linked directly to the control element.

A controller 97 according to another embodiment is shown in FIGS. 23a to 23e. The controller 97 includes an actuator, for moving outer tubes 931 relative to the central tube 921, in combination with features of an introducer, to assist in locating the guidewires in the central and outer lumens of the central and outer tubes 921, 922, in a similar manner to the introducers described above.

Figure 23A:
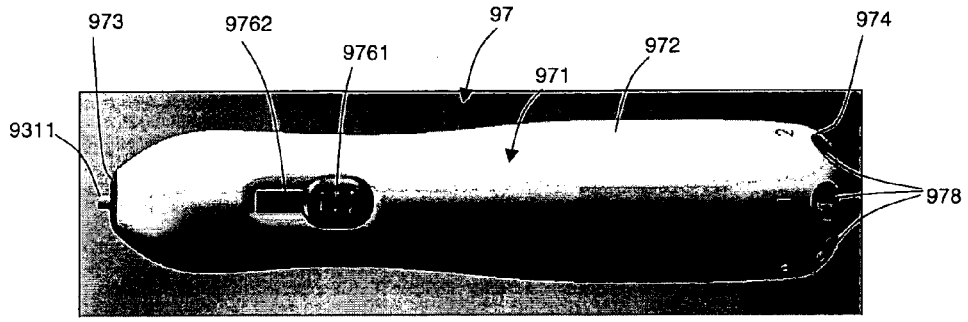
FIGS. 23a to 23e show a top view, side view, oblique view, proximal end view and distal end view, respectively, of a fourth example of a controller for controlling movement of the wedge element of the catheter apparatus of FIGS. 11a and 11b.
Figure 23B:
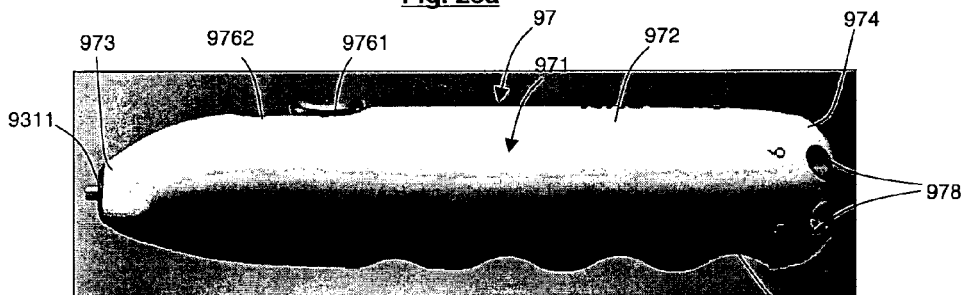
Figure 23C:
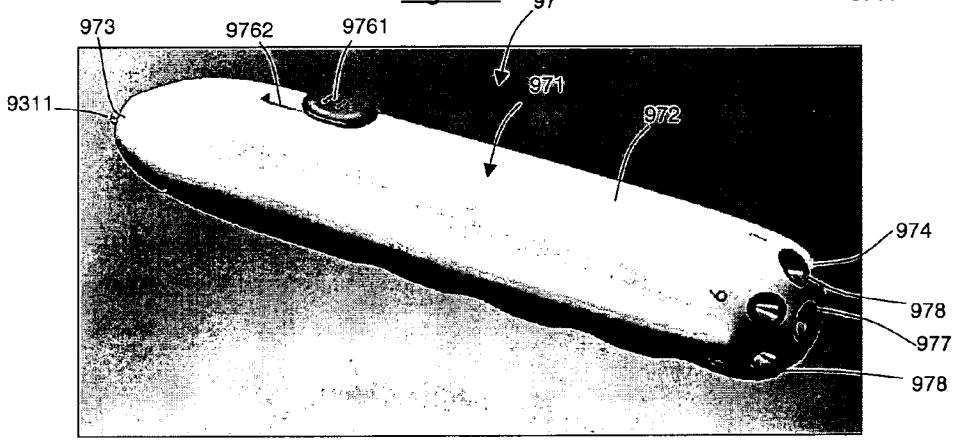
Figure 23D:
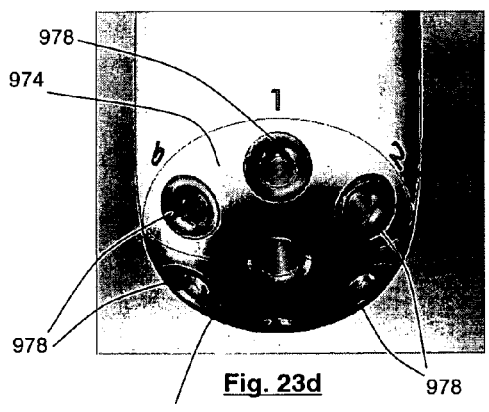
Figure 23E:
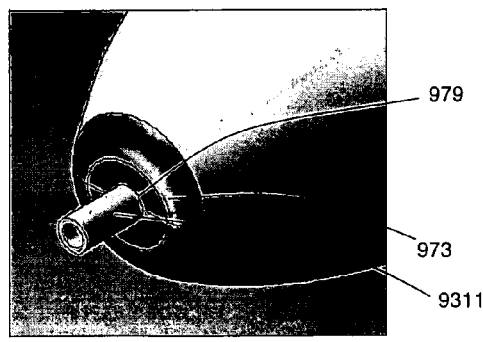

In more detail, the controller 97 comprises an elongate housing 971, having sidewalls 972 extending between distal and proximal ends 973, 974. A button 9761 or lever is provided that is slidable within a slot 9762 in the sidewalls 972 of the housing 971. The button 9761 is part of an actuator mechanism 976, discussed further below. With reference to FIG. 23d, at the proximal end 974 of the housing 971, a central input opening 977 is provided for a guidewire to enter the central lumen provided by the central tube 921, and outer input openings 978, are provided for a guidewire to enter the outer lumens provided by the outer tubes 931. Although not shown, the input openings 977, 978 may have closure means to prevent fluid, e.g. blood, leaking through them from a patient. For example, the openings 977, 978 may have valves or luer lock additions. This arrangement may also permit flushing of the tubes 921, 931 prior to insertion of the catheter 92 in a patient, or allow for 'blowing off' of the device whilst the guidewires(s) are in place.

Numbering is provided on the housing, adjacent each outer input opening, to distinguish the outer input openings from one another. At the distal end of the housing 971, a distal end opening 979 is provided through which the catheter 92, comprising the central and outer tubes 921, 931, projects from the housing. A hand grip 9711 is provided on the bottom of the housing 971.

The actuator mechanism 976 can be seen in FIGS. 24 to 26b. The button 9761 is pivotally and slidably mounted to an arm 9763 at a first pivot point A. This is achieved by locating a pin 9764 connected to the button 9761 in a first slot 9765 provided in the arm 9763. The arm 9763 is pivotally mounted to a support 9766, fixed to the housing 971, at a second pivot point B. The central tube 921 is fixed to the housing 971 adjacent the central input opening 977 and travels through the housing 971, in the elongation direction of the housing, in a substantially straight line. The outer tubes 931 are fixed to the housing 971 adjacent respective outer input openings 978, and travel in the housing along substantially curved paths to a convergent point where, along with the central tube 921, they extend through a sheath 9311 located in the housing 971. The sheath 9311 is fixed to the outer tubes 931 but not the central tube 921. Since the outer tubes 931 are flexible and follow curved paths before extending into the sheath 9311, movement of the sheath 9311 and the outer tubes 931 is possible relative to the housing 971 and relative to the central tube 921. The sheath 9311 is pivotally and slidably mounted to the arm 9763 at a pivot point C, intermediate the first and second pivot points A, B. This is achieved by locating a pin 9767 fixed to the sheath 9311 in a second slot 9768 provided in the arm 9763.

When the button 9761 is caused to slide in the slot 9762 of the housing 971, in the elongation direction of the housing 971, the arrangement is such that the button 9761 forces the arm 9763 to rotate about point B, which also forces the sheath 9311 and outer tubes 931 to move in the elongation direction of the housing 971, relative to the fixed central tube 921, causing the wedge element 94 connected to the central tube 921 at the tip region 901 of the apparatus to move relative to the outer tubes 931, changing the separation of the distal end openings 932 of the outer tubes 931, as discussed above. The movement of the button 9761 and arm 9763 can be seen by comparing FIGS. 26a and 26b. The actuator mechanism 976 may be arranged so as to prevent accidental removal of the catheter 92 from the patient with the tip region 901 expanded (i.e. with the distal end openings 932 substantially separated).

Since the outer tubes 931 are connected to the arm 9763 via the sheath 9311 at a position closer to pivot point B than the button 9761, as the arm 9763 rotates, the distance that the outer tubes 931 travel is less than that of the button 9761. This scaling of movement between the button 9761 and the outer tubes 931 provides for more precise control of the relative movement of the wedge element 94 and the outer tubes 931. In this embodiment, there is a 4:1 movement ratio between the button 9761 and the outer tubes 931. Accordingly, when the button 9761 is moved 20 mm along the slot 9762, in the elongation direction of the housing 971, the outer tubes 931 move only 5 mm in the elongation direction of the housing 971. It is considered that similar scaling arrangements could be applied to the controllers discussed above with respect to the FIGS. 20 to 22.

The button 9761 and the outer tubes 931 are both pivotally and slidably mounted to the arm 9763 as described above so that, when the arm 9763 rotates about pivot point B, the button 9761 can maintain the same orientation relative to the slot 9762 in the housing 971 and sheath 9311 and the outer tubes 931 can maintain the same orientation relative to the distal end opening 979 of the housing and the central tube 921, preventing possible jamming and/or breakage of the controller 97.

The invention claimed is:

1. A catheter apparatus, the catheter apparatus having a proximal end and a distal end, the distal end being for insertion into a patient's body, the catheter apparatus comprising:
   a catheter having a proximal end and a distal end;
   first and second lumens for accommodating first and second guidewires respectively, each lumen comprising a distal opening, the distal openings of the first and second lumens being moveable relative to each other; and
   an actuator for controllably changing the separation between the distal openings of the first and second lumens;
   wherein a plurality of the first lumen and/or a plurality of the second lumen are provided, to provide a plurality of selectable lumens for accommodating the first and/or second guidewires;
   wherein the apparatus comprises a first lumen and a plurality of second lumens and the distal openings of the second lumens are arranged around the distal opening of the first lumen, and the actuator for controllably changing the separation between the distal openings of the lumens is arranged to move the distal openings of the second lumens in radial directions from the distal opening of the first lumen.

2. The catheter apparatus of claim 1, wherein the changing of the separation between the distal openings of the first and second lumens is in a direction substantially perpendicular to the elongation direction of the catheter.

3. The apparatus of claim 1, further comprising first and second guidewires disposed in the first and second lumens respectively.

4. The apparatus of claim 1, wherein the one or both of the first and second lumens is provided within the catheter.

5. The apparatus of claim 4, wherein the distal openings of the first and/or second lumens provided within the catheter are provided at the distal end of the catheter.

6. The apparatus of claim 1, wherein the catheter has a tip region at its distal end comprising first and second sections, the first and second sections being moveable relative to each other, the distal opening of at least one of the first and second lumens being provided in one of the first and second sections, wherein the actuator is arranged to change the separation of the first and second sections in order to change the separation of the distal openings of the first and second lumens.

7. The apparatus of claim 6, wherein the distal opening of the first lumen is provided in the first section and the distal opening of the second lumen is provided in the second section.

8. The apparatus of claim 6, wherein the tip region of the catheter has side walls that are split to permit separation of the first and second sections.

9. The apparatus of claim 6, wherein the tip region of the catheter has side walls which are flexible, to permit separation of the first and second sections.

10. The apparatus of claim 4, wherein one of the first and second lumens is provided in an additional section connected to the catheter, which additional section extends alongside the catheter from a position at the distal end of the catheter, along all or part of the length of the catheter.

11. The apparatus of claim 1, wherein the distal opening of the second lumens are arranged in a circle around the distal opening of the first lumen.

12. A catheter apparatus, the catheter apparatus having a proximal end and a distal end, the distal end being for insertion into a patient's body, the catheter apparatus comprising:
a catheter having a proximal end and a distal end, the distal end being for insertion into a patient's body, first and second guidewires, the guidewires arranged to project at the distal end of the catheter apparatus, and an actuator for controllably changing the separation between the guidewires at the distal end of the catheter apparatus;
wherein the actuator comprises an expandable element.

13. The catheter apparatus of claim 12, wherein the changing of the separation between the guidewires is in a direction substantially perpendicular to the elongation direction of the catheter.

14. The catheter apparatus of claim 12, wherein the catheter apparatus comprises first and second lumens and the first and second guidewires are located in the first and second lumens respectively.

15. The apparatus claim 12, wherein the catheter is rotatable about the longitudinal axis of the first guidewire or second guidewire.

16. The apparatus of claim 12, wherein, upon expansion, the expandable element pushes or pulls the first and second sections, the first and second lumens and/or the first and second guidewires to change the separation of the distal openings of the first and second lumens and/or the first and second guidewires.

17. The apparatus of claim 12, wherein the expandable element is an inflatable balloon.

18. The apparatus of claim 12, wherein the actuator comprises a moveable wedge element.

19. The apparatus of claim 18, wherein the wedge element is moveable into a position between the first and second sections, the first and second lumens and/or the first and second guidewires in order to move the distal openings of the first and second lumens and/or the first and second guidewires apart, and moveable away from this position in order to permit the distal openings of the first and second lumens and/or the first and second guidewires to move closer together.

20. The apparatus of claim 19, wherein the first and second lumens are provided by respective tubes and the wedge element comprises a plurality of channels for guiding the tubes providing the second lumens.

21. The apparatus of claim 19, wherein the lumens are provided by respective tubes and the wedge element comprises a central conduit for accommodating the tube providing the first lumen.

22. The apparatus of claim 12, wherein the actuator comprises a rotatable cam element.

23. The apparatus of claim 22, wherein the rotatable cam element is located between the first and second sections, the first and second lumens and/or the first and second guidewires and shaped such that, upon rotation, its dimension across an axis between the first and second sections, the first and second lumens and/or the first and second guidewires varies, in order to change the separation of the first and second lumens and/or the first and second guidewires.

24. The apparatus of claim 12, wherein the actuator comprises at least two magnetic elements, at least one of the magnetic elements being moveable such that the magnetic poles of the at least two magnetic elements can be brought in and out of alignment.

25. The apparatus of claim 24, comprising a first magnet located adjacent the first lumen and/or first guidewire, a second magnet located adjacent the second lumen and/or second guidewire, and a third magnet located between the first and second magnets and rotatable between first and second positions, wherein, in the first position, the poles of the third magnet are located adjacent opposite poles of the first and second magnets such that the first and second magnets are attracted toward the third magnet and, in the second position, the poles of the third magnet are adjacent corresponding poles of the first and second magnets, such that the first and second magnets are repelled from the third magnet.

26. The apparatus of claim 12, comprising a controller for controlling movement of the actuator, the controller comprising a controller housing and an actuation element.

27. The apparatus of claim 26, wherein the controller housing comprises a hand grip.

28. The apparatus of claim 12, comprising a guidewire introducer to assist in locating the guidewires in the first and second lumens, the introducer comprising an introducer housing having a plurality of conduits therein, each conduit being adapted to channel the guidewires into a respective one of the first and second lumens, the guidewires being extendible into the conduits via input openings on an end face of the introducer housing.

29. The apparatus of claim 28, wherein the end face of the introducer housing comprises a plurality of steps, each input opening being located on a different step.

30. The apparatus of claim 28, wherein the introducer housing comprises a plurality of protrusions arranged in clusters adjacent each of the input openings, the number of protrusions in each cluster being distinct to the input opening adjacent the cluster.

31. The apparatus of claim 12, wherein one of the first and second guidewires is for guiding the catheter to a destination in the patient's body and the other is for probing an occlusion in a blood vessel.

32. The apparatus of claim 31, wherein the occlusion is a chronic total occlusion.

33. The apparatus of claim 31, wherein the guidewire for guiding the catheter to the destination in the patient's body comprises first and second guidewire sections, the first guidewire section projecting from the distal end of the catheter and having a spiral shape, and the second guidewire section, connected to the first guidewire section, being located within the first lumen and having a substantially linear shape.

* * * * *

UNITED STATES PATENT AND TRADEMARK OFFICE
CERTIFICATE OF CORRECTION

PATENT NO. : 8,608,688 B2
APPLICATION NO. : 12/738831
DATED : December 17, 2013
INVENTOR(S) : Jain et al.

It is certified that error appears in the above-identified patent and that said Letters Patent is hereby corrected as shown below:

Title Page, Item (12) delete "Jain" and insert --Jain et al.--.

Title Page, Item (75) Inventor, should read

--(75) Inventors: Ajay Kumar Jain, London (GB); Martin T. Rothman, London (GB)--.

Signed and Sealed this
Eighth Day of March, 2016

Michelle K. Lee
*Director of the United States Patent and Trademark Office*